United States Patent [19]
Cowart et al.

[11] Patent Number: 5,861,294
[45] Date of Patent: *Jan. 19, 1999

[54] ADENOSINE KINASE POLYPEPTIDES

[75] Inventors: Marlon Daniel Cowart, Round Lake Beach; Donald N. Halbert, Libertyville; James F. Kerwin, Jr., Grayslake; Teresa McNally, Gurnee, all of Ill.

[73] Assignee: Abbott Laboratories, Abbott Park, Ill.

[*] Notice: This patent issued on a continued prosecution application filed under 37 CFR 1.53(d), and is subject to the twenty year patent term provisions of 35 U.S.C. 154(a)(2).

[21] Appl. No.: 479,614

[22] Filed: Jun. 7, 1995

[51] Int. Cl.$^6$ .......................... C12N 15/00; C12N 15/85; C12N 15/63; C12N 9/12

[52] U.S. Cl. .................. 435/194; 435/325; 435/320.1; 435/69; 536/23.1; 536/23.2; 536/24.3

[58] Field of Search .................. 424/178.1; 435/7.1, 435/69.1, 71.1, 194, 252.3, 320.1, 325; 536/24.3, 23.1, 23.2

[56] References Cited

PUBLICATIONS

Written Opinion corresponding to PCT/US96/08097 (1997).
International Search Report corresponding to PCT/US96/08097 (1997).
Andres et al (1979). J. Biol Chem 254(22):11388–11393. "Purification and Properties of Human placental adenosine kinase".
Cloning of Human Adeonsine Kinase cDNA: Sequence Similarity to Microbial Ribokinases and Fructokinases; Prot Natl. Acad Sci USA vol. 93, pp. 1232–1237. Feb. 1996.
Cloning of Human Adenosine Kinase cDNA: Sequence Similarity to Microbial Ribokinases and Fructokinases; Prot Natl. Acad Sci USA vol. 93, pp. 1232–1237, Feb. 1996, Spychala et al.

Chang, C.–H. et al., J. Biol. Chem., vol. 255, No. 6, pp. 2366–2370, 1980.
Uitendaal, M. et al., Adv. Exp. Med. Biol., vol. 122B, pp. 409–414, 1980.
Bork, Peer et al. "Convergent evolution of similar enzymatic function on different protein folds: The hexokinase, ribokinase, and galactokinase families of sugar kinases." *Protein Science* vol. 2 (1993): pp. 31–40.
Juranka, Peter et al. "Analysis of Adenosine Kinase Mutants of Baby Hamster Kidney Cells Using Affinity–purified Antibody." *The Journal of Biological Chemistry* vol. 260. No. 12 (Jun. 25, 1985): pp. 7738–7743.
Pang, Jesse et al. "Imbalance of Purine Nucleotides in Alanosine–Resistant Baby Hamster Kidney Cells." *Somatic Cell and Molecular Genetics* vol. 15, No. 2 (1989): pp. 101–111.
Samuelson, Linda C. et al., "Cytological Localization of Adenosine Kinase, Nucleoside Phosphorylase–1, and Esterase–10 Genes on Mouse Chromosome 14." *Somatic Cell and Molecular Genetics* vol. 11, No. 2 (1985): pp. 157–165.
Yamada, Yasukazu et al. "Adenosine Kinase from Human Liver." *Biochimica et Biophysica Acta* vol. 660 (1981): pp. 36–43.
Yamada, Yasukazu et al. "Differences of Adenosine Kinases from Various Mammalian Tissues." *Comp. Biochem. Physiol.* vol. 71B, No. 3 (1982): pp. 367–372.

*Primary Examiner*—Eric Grimes
*Assistant Examiner*—Peter P. Tung
*Attorney, Agent, or Firm*—Thomas D. Brainard; Mark R. Bach; Mimi C. Goller

[57] ABSTRACT

The present invention provides an adenosine kinase protein having an identified structural formula. The identified protein or similar adenosine kinase proteins having residues as claimed and recited herein may be isolated and purified from natural sources or produced by recombinant DNA technology.

22 Claims, 12 Drawing Sheets

```
                        *
      GGGATTAGAGTCAAGATGGCAGCTGCGGACGAGCCGAAGCCCAAGAAGCTCAAGGTGGAA
  1   ---------+---------+---------+---------+---------+---------+  60
      CCCTAATCTCAGTTCTACCGTCGACGCCTGCTCGGCTTCGGGTTCTTCGAGTTCCACCTT

M  A  A  A  D  E  P  K  P  K  K  L  K  V  E   -

GCGCCAGAAGCGCTGAGTGAAAATGTGCTGTTTGGAATGGGGAATCCTCTTCTTGACATC
 61   ---------+---------+---------+---------+---------+---------+ 120
      CGCGGTCTTCGCGACTCACTTTTACACGACAAACCTTACCCCTTAGGAGAAGAACTGTAG

A  P  E  A  L  S  E  N  V  L  F  G  M  G  N  P  L  L  D  I  -

TCTGCTGTGGTAGACAAAGATTTCCTTGATAAGTATTCTCTGAAACCAAACGACCAGATC
121   ---------+---------+---------+---------+---------+---------+ 180
      AGACGACACCATCTGTTTCTAAAGGAACTATTCATAAGAGACTTTGGTTTGCTGGTCTAG

S  A  V  V  D  K  D  F  L  D  K  Y  S  L  K  P  N  D  Q  I  -

TTGGCCGAAGACAAGCACAAGGAATTGTTTGATGAACTTGTAAAAAAATTCAAAGTTGAA
181   ---------+---------+---------+---------+---------+---------+ 240
      AACCGGCTTCTGTTCGTGTTCCTTAACAAACTACTTGAACATTTTTTAAGTTTCAACTT

L  A  E  D  K  H  K  E  L  F  D  E  L  V  K  K  F  K  V  E  -

TATCATGCCGGTGGGTCCACGCAGAATTCAATGAAAGTGGCTCAGTGGATGATTCAGGAG
241   ---------+---------+---------+---------+---------+---------+ 300
      ATAGTACGGCCACCCAGGTGCGTCTTAAGTTACTTTCACCGAGTCACCTACTAAGTCCTC

Y  H  A  G  G  S  T  Q  N  S  M  K  V  A  Q  W  M  I  Q  E  -

CCACACAGAGCAGCAACGTTCTTCGGATGCATTGGGATAGATAAGTTCGGGGAGATCCTG
301   ---------+---------+---------+---------+---------+---------+ 360
      GGTGTGTCTCGTCGTTGCAAGAAGCCTACGTAACCCTATCTATTCAAGCCCCTCTAGGAC

P  H  R  A  A  T  F  F  G  C  I  G  I  D  K  F  G  E  I  L  -

AAGAGCAAAGCCGCAGATGCACACGTGGACGCCCATTACTATGAGCAGAACGAGCAGCCC
361   ---------+---------+---------+---------+---------+---------+ 420
      TTCTCGTTTCGGCGTCTACGTGTGCACCTGCGGGTAATGATACTCGTCTTGCTCGTCGGG

K  S  K  A  A  D  A  H  V  D  A  H  Y  Y  E  Q  N  E  Q  P  -

ACAGGAACGTGCGCTGCATGCATCACCGGTGGCAACCGGTCTCTTGTTGCTAACCTTGCT
421   ---------+---------+---------+---------+---------+---------+ 480
      TGTCCTTGCACGCGACGTACGTAGTGGCCACCGTTGGCCAGAGAACAACGATTGGAACGA

T  G  T  C  A  A  C  I  T  G  G  N  R  S  L  V  A  N  L  A  -

GCCGCCAATTGTTATAAGAAAGAAAAGCACCTTGATCTGGAGAACAACTGGATGTTGGTA
481   ---------+---------+---------+---------+---------+---------+ 540
      CGGCGGTTAACAATATTCTTTCTTTTCGTGGAACTAGACCTCTTGTTGACCTACAACCAT

A  A  N  C  Y  K  K  E  K  H  L  D  L  E  N  N  W  M  L  V  -

GAGAAAGCCAGAGTTTACTACATAGCTGGCTTCTTTCTCACCGTCTCCCCAGAGTCAGTG
541   ---------+---------+---------+---------+---------+---------+ 600
      CTCTTTCGGTCTCAAATGATGTATCGACCGAAGAAAGAGTGGCAGAGGGGTCTCAGTCAC

```
         TTGAAAGTGGCTCGCTATGCTGCCGAGAACAACAGGACCTTCACTCTTAACCTGTCCGCA
    601  ---------+---------+---------+---------+---------+---------+  660
         AACTTTCACCGAGCGATACGACGGCTCTTGTTGTCCTGGAAGTGAGAATTGGACAGGCGT

L  K  V  A  R  Y  A  A  E  N  N  R  T  F  T  L  N  L  S  A  -

CCGTTCATTAGCCAGTTCTTCAAGGAAGCCTTGATGGAAGTCATGCCTTATGTTGACATC
    661  ---------+---------+---------+---------+---------+---------+  720
         GGCAATGAATCGGTCAAGAAGTTCCTTCGGAACTACCTTCAGTACGGAATACAACTGTAG

P  F  I  S  Q  F  F  K  E  A  L  M  E  V  M  P  Y  V  D  I  -

CTCTTTGGAAATGAGACGGAGGCTGCCACTTTTGCTAGAGAGCAAGGCTTTGAGACTAAA
    721  ---------+---------+---------+---------+---------+---------+  780
         GAGAAACCTTTACTCTGCCTCCGACGGTGAAAACGATCTCTCGTTCCGAAACTCTGATTT

L  F  G  N  E  T  E  A  A  T  F  A  R  E  Q  G  F  E  T  K  -

GACATTAAAGAAATAGCCAGAAAGACGCAGGCTCTTCCAAAGGTGAACTCGAAGAGGCAG
    781  ---------+---------+---------+---------+---------+---------+  840
         CTGTAATTTCTTTATCGGTCTTTCTGCGTCCGAGAAGGTTTCCACTTGAGCTTCTCCGTC

D  I  K  E  I  A  R  K  T  Q  A  L  P  K  V  N  S  K  R  Q  -

AGGACCGTGATCTTCACCCAAGGGAGAGATGACACTATAGTAGCTACAGGAAATGATGTC
    841  ---------+---------+---------+---------+---------+---------+  900
         TCCTGGCACTAGAAGTGGGTTCCCTCTCTACTGTGATATCATCGATGTCCTTTACTACAG

R  T  V  I  F  T  Q  G  R  D  D  T  I  V  A  T  G  N  D  V  -

ACTGCTTTCCCTGTCTTGGATCAAAACCAGGAAGAGATCGTTGACACCAATGGAGCTGGA
    901  ---------+---------+---------+---------+---------+---------+  960
         TGACGAAAGGGACAGAACCTAGTTTTGGTCCTTCTCTAGCAACTGTGGTTACCTCGACCT

T  A  F  P  V  L  D  Q  N  Q  E  E  I  V  D  T  N  G  A  G  -

GATGCATTTGTAGGAGGGTTTCTGTCTCAGCTGGTCTCCAACAAGCCTCTGACTGAATGC
    961  ---------+---------+---------+---------+---------+---------+  1020
         CTACGTAAACATCCTCCCAAAGACAGAGTCGACCAGAGGTTGTTCGGAGACTGACTTACG

D  A  F  V  G  G  F  L  S  Q  L  V  S  N  K  P  L  T  E  C  -

ATCCGGGCCGGGCACTATGCAGCGAGCGTCATCATTAGGCGAACTGGCTGTACTTTTCCT
   1021  ---------+---------+---------+---------+---------+---------+  1080
         TAGGCCCGGCCCGTGATACGTCGCTCGCAGTAGTAATCCGCTTGACCGACATGAAAAGGA

I  R  A  G  H  Y  A  A  S  V  I  I  R  R  T  G  C  T  F  P  -

GAGAAGCCAAACTTCCACTGACGGAAGAAAAGCAACTCAGGCAATCACTAGTGCGGCCGC
   1081  ---------+---------+---------+---------+---------+---------+  1140
         CTCTTCGGTTTGAAGGTGACTGCCTTCTTTTCGTTGAGTCCGTTAGTGATCACGCCGGCG

E  K  P  N  F  H  *  (SEQ ID NO:2)

CTGCAGGTCGACCATATGGGAGAGCTCCCAACGCGTTGGATGCATAGCTT   (SEQ ID NO:1)
   1141  ---------+---------+---------+---------+---------+  1190
         GACGTCCAGCTGGTATACCCTCTCGAGGGTTGCGCAACCTACGTATCGAA   (SEQ ID NO:3)
```

Fig. 2b

```
     GCCGGGAAGCAGTTGCTGTGGTACCTGCTGCTGCCCGAGCGGACGTAGAGCATCGGACGC
  1  ------------+---------+---------+---------+---------+---------+  60
     CGGCCCTTCGTCAACGACACCATGGACGACGACGGGCTCGCCTGCATCTCGTAGCCTGCG
                                            *
     GGCCGCCGTGGCGCTGGGCAGGAGGGCGAAGCCATGACGTCAGTCAGAGAAAATATTCTC
 61  ------------+---------+---------+---------+---------+---------+ 120
     CCGGCGGCACCGCGACCCGTCCTCCCGCTTCGGTACTGCAGTCAGTCTCTTTTATAAGAG
                                         M  T  S  V  R  E  N  I  L  -

TTTGGAATGGGAAATCCTCTGCTTGACATCTCTGCTGTAGTGGACAAAGATTTCCTTGAT
121  ------------+---------+---------+---------+---------+---------+ 180
     AAACCTTACCCTTTAGGAGACGAACTGTAGAGACGACATCACCTGTTTCTAAAGGAACTA

F  G  M  G  N  P  L  L  D  I  S  A  V  V  D  K  D  F  L  D  -

AAGTATTCTCTGAAACCAAATGACCAAATCTTGGCTGAAGACAAACACAAGGAACTGTTT
181  ------------+---------+---------+---------+---------+---------+ 240
     TTCATAAGAGACTTTGGTTTACTGGTTTAGAACCGACTTCTGTTTGTGTTCCTTGACAAA

K  Y  S  L  K  P  N  D  Q  I  L  A  E  D  K  H  K  E  L  F  -

GATGAACTTGTGAAAAAATTCAAAGTCGAATATCATGCTGGTGGCTCTACCCAGAATTCA
241  ------------+---------+---------+---------+---------+---------+ 300
     CTACTTGAACACTTTTTTAAGTTTCAGCTTATAGTACGACCACCGAGATGGGTCTTAAGT

D  E  L  V  K  K  F  K  V  E  Y  H  A  G  G  S  T  Q  N  S  -

ATTAAAGTGGCTCAGTGGATGATTCAACAGCCACACAAAGCAGCAACATTTTTTGGATGC
301  ------------+---------+---------+---------+---------+---------+ 360
     TAATTTCACCGAGTCACCTACTAAGTTGTCGGTGTGTTTCGTCGTTGTAAAAAACCTACG

I  K  V  A  Q  W  M  I  Q  Q  P  H  K  A  A  T  F  F  G  C  -

ATTGGGATAGATAAATTTGGGGAGATCCTGAAGAGAAAAGCTGCTGAAGCCCATGTGGAT
361  ------------+---------+---------+---------+---------+---------+ 420
     TAACCCTATCTATTTAAACCCCTCTAGGACTTCTCTTTTCGACGACTTCGGGTACACCTA

I  G  I  D  K  F  G  E  I  L  K  R  K  A  A  E  A  H  V  D  -

GCTCATTACTACGAGCAGAATGAGCAGCCAACAGGAACTTGTGCTGCATGCATCACTGGT
421  ------------+---------+---------+---------+---------+---------+ 480
     CGAGTAATGATGCTCGTCTTACTCGTCGGTTGTCCTTGAACACGACGTACGTAGTGACCA

A  H  Y  Y  E  Q  N  E  Q  P  T  G  T  C  A  A  C  I  T  G  -

GACAACAGGTCCCTCATAGCTAATCTTGCTGCTGCCAATTGTTATAAAAAGGAAAAACAT
481  ------------+---------+---------+---------+---------+---------+ 540
     CTGTTGTCCAGGGAGTATCGATTAGAACGACGACGGTTAACAATATTTTCCTTTTTGTA

D  N  R  S  L  I  A  N  L  A  A  A  N  C  Y  K  K  E  K  H  -

CTTGATCTGGAGAAAAACTGGATGTTGGTAGAAAAAGCAAGAGTTTGTTATATAGCAGGC
541  ------------+---------+---------+---------+---------+---------+ 600
     GAACTAGACCTCTTTTTGACCTACAACCATCTTTTTCGTTCTCAAACAATATATCGTCCG

```
          TTTTTTCTTACAGTTTCCCCAGAGTCAGTATTAAAGGTGGCTCACCATGCTTCTGAAAAC
601       ----------+---------+---------+---------+---------+---------+ 660
          AAAAAAGAATGTCAAAGGGGTCTCAGTCATAATTTCCACCGAGTGGTACGAAGACTTTTG

F  F  L  T  V  S  P  E  S  V  L  K  V  A  H  H  A  S  E  N   -

AACAGGATTTTCACTTTGAATCTATCTGCACCGTTTATTAGCCAGTTCTACAAGGAATCA
661       ----------+---------+---------+---------+---------+---------+ 720
          TTGTCCTAAAAGTGAAACTTAGATAGACGTGGCAAATAATCGGTCAAGATGTTCCTTAGT

N  R  I  F  T  L  N  L  S  A  P  F  I  S  Q  F  Y  K  E  S   -

TTGATGAAAGTTATGCCTTATGTTGATATACTTTTTGGAAATGAGACAGAAGCTGCCACT
721       ----------+---------+---------+---------+---------+---------+ 780
          AACTACTTTCAATACGGAATACAACTATATGAAAAACCTTTACTCTGTCTTCGACGGTGA

L  M  K  V  M  P  Y  V  D  I  L  F  G  N  E  T  E  A  A  T   -

TTTGCTAGAGAGCAAGGCTTTGAGACTAAAGACATTAAAGAGATAGCCAAAAAGACACAA
781       ----------+---------+---------+---------+---------+---------+ 840
          AAACGATCTCTCGTTCCGAAACTCTGATTTCTGTAATTTCTCTATCGGTTTTTCTGTGTT

F  A  R  E  Q  G  F  E  T  K  D  I  K  E  I  A  K  K  T  Q   -

GCCCTGCCAAAGATGAACTCAAAGAGGCAGCGAATCGTGATCTTCACCCAAGGGAGAGAT
841       ----------+---------+---------+---------+---------+---------+ 900
          CGGGACGGTTTCTACTTGAGTTTCTCCGTCGCTTAGCACTAGAAGTGGGTTCCCTCTCTA

A  L  P  K  M  N  S  K  R  Q  R  I  V  I  F  T  Q  G  R  D   -

GACACTATAATGGCTACAGAAAGTGAAGTCACTGCTTTTGCTGTCTTGGATCAAGACCAG
901       ----------+---------+---------+---------+---------+---------+ 960
          CTGTGATATTACCGATGTCTTTCACTTCAGTGACGAAAACGACAGAACCTAGTTCTGGTC

D  T  I  M  A  T  E  S  E  V  T  A  F  A  V  L  D  Q  D  Q   -

AAAGAAATTATTGATACCAATGGAGCTGGAGATGCATTTGTTGGAGGTTTTCTGTCTCAA
961       ----------+---------+---------+---------+---------+---------+ 1020
          TTTCTTTAATAACTATGGTTACCTCGACCTCTACGTAAACAACCTCCAAAAGACAGAGTT

K  E  I  I  D  T  N  G  A  G  D  A  F  V  G  G  F  L  S  Q   -

CTGGTCTCTGACAAGCCTCTGACTGAATGTATCCGTGCTGGCCACTATGCAGCAAGCATC
1021      ----------+---------+---------+---------+---------+---------+ 1080
          GACCAGAGACTGTTCGGAGACTGACTTACATAGGCACGACCGGTGATACGTCGTTCGTAG

L  V  S  D  K  P  L  T  E  C  I  R  A  G  H  Y  A  A  S  I   -

ATAATTAGACGGACTGGCTGCACCTTTCCTGAGAAGCCAGACTTCCACTGATGGAAGAGC
1081      ----------+---------+---------+---------+---------+---------+ 1140
          TATTAATCTGCCTGACCGACGTGGAAAGGACTCTTCGGTCTGAAGGTGACTACCTTCTCG

I  I  R  R  T  G  C  T  F  P  E  K  P  D  F  H  *  (SEQ ID NO:5)

TGAAAACACAAGCCCAGGAGTGCAGACACCCC    (SEQ ID NO:4)
1141      ----------+---------+---------+-- 1172
          ACTTTTGTGTTCGGGTCCTCACGTCTGTGGGG    (SEQ ID NO:6)
```

Fig. 3b

```
                                                                  *
     GTGGATGGCAGAGGTGGGCTGTAGAGCCAAAGTGGGGTGGGAGCGCGAAGATGGCTGCTG
  1  ---------+---------+---------+---------+---------+---------+  60
     CACCTACCGTCTCCACCCGACATCTCGGTTTCACCCCACCCTCGCGCTTCTACCGACGAC

M  A  A  A -

CTGAGGAGGAGCCGAAGCCCAAAAAGCTGAAGGTGGAGGCGCCGCAAGCGCTGAGAGAAA
  61 ---------+---------+---------+---------+---------+---------+ 120
     GACTCCTCCTCGGCTTCGGGTTTTTCGACTTCCACCTCCGCGGCGTTCGCGACTCTCTTT

E  E  E  P  K  P  K  K  L  K  V  E  A  P  Q  A  L  R  E  N -

ATATTCTCTTTGGAATGGGAAATCCTCTGCTTGACATCTCTGCTGTAGTGGACAAAGATT
 121 ---------+---------+---------+---------+---------+---------+ 180
     TATAAGAGAAACCTTACCCTTTAGGAGACGAACTGTAGAGACGACATCACCTGTTTCTAA

I  L  F  G  M  G  N  P  L  L  D  I  S  A  V  V  D  K  D  F -

TCCTTGATAAGTATTCTCTGAAACCAAATGACCAAATCTTGGCTGAAGACAAACACAAGG
 181 ---------+---------+---------+---------+---------+---------+ 240
     AGGAACTATTCATAAGAGACTTTGGTTTACTGGTTTAGAACCGACTTCTGTTTGTGTTCC

L  D  K  Y  S  L  K  P  N  D  Q  I  L  A  E  D  K  H  K  E -

AACTGTTTGATGAACTTGTGAAAAAATTCAAAGTCGAATATCATGCTGGTGGCTCTACCC
 241 ---------+---------+---------+---------+---------+---------+ 300
     TTGACAAACTACTTGAACACTTTTTTAAGTTTCAGCTTATAGTACGACCACCGAGATGGG

L  F  D  E  L  V  K  K  F  K  V  E  Y  H  A  G  G  S  T  Q -

AGAATTCAATTAAAGTGGCTCAGTGGATGATTCAACAGCCACACAAAGCAGCAACATTTT
 301 ---------+---------+---------+---------+---------+---------+ 360
     TCTTAAGTTAATTTCACCGAGTCACCTACTAAGTTGTCGGTGTGTTTCGTCGTTGTAAAA

N  S  I  K  V  A  Q  W  M  I  Q  Q  P  H  K  A  A  T  F  F -

TTGGATGCATTGGGATAGATAAATTTGGGGAGATCCTGAAGAGAAAAGCTGCTGAAGCCC
 361 ---------+---------+---------+---------+---------+---------+ 420
     AACCTACGTAACCCTATCTATTTAAACCCCTCTAGGACTTCTCTTTTCGACGACTTCGGG

G  C  I  G  I  D  K  F  G  E  I  L  K  R  K  A  A  E  A  H -

ATGTGGATGCTCATTACTACGAGCAGAATGAGCAGCCAACAGGAACTTGTGCTGCATGCA
 421 ---------+---------+---------+---------+---------+---------+ 480
     TACACCTACGAGTAATGATGCTCGTCTTACTCGTCGGTTGTCCTTGAACACGACGTACGT

V  D  A  H  Y  Y  E  Q  N  E  Q  P  T  G  T  C  A  A  C  I -

TCACTGGTGACAACAGGTCCCTCATAGCTAATCTTGCTGCTGCCAATTGTTATAAAAAGG
 481 ---------+---------+---------+---------+---------+---------+ 540
     AGTGACCACTGTTGTCCAGGGAGTATCGATTAGAACGACGACGGTTAACAATATTTTTCC

T  G  D  N  R  S  L  I  A  N  L  A  A  A  N  C  Y  K  K  E -

AAAAACATCTTGATCTGGAGAAAAACTGGATGTTGGTAGAAAAAGCAAGAGTTTGTTATA
 541 ---------+---------+---------+---------+---------+---------+ 600
     TTTTTGTAGAACTAGACCTCTTTTTGACCTACAACCATCTTTTTCGTTCTCAAACAATAT

```
     TAGCAGGCTTTTTTCTTACAGTTTCCCCAGAGTCAGTATTAAAGGTGGCTCACCATGCTT
601  ---------+---------+---------+---------+---------+---------+ 660
     ATCGTCCGAAAAAGAATGTCAAAGGGGTCTCAGTCATAATTTCCACCGAGTGGTACGAA

A  G  F  F  L  T  V  S  P  E  S  V  L  K  V  A  H  H  A  S -

CTGAAAACAACAGGATTTTCACTTTGAATCTATCTGCACCGTTTATTAGCCAGTTCTACA
661  ---------+---------+---------+---------+---------+---------+ 720
     GACTTTTGTTGTCCTAAAAGTGAAACTTAGATAGACGTGGCAAATAATCGGTCAAGATGT

E  N  N  R  I  F  T  L  N  L  S  A  P  F  I  S  Q  F  Y  K -

AGGAATCATTGATGAAAGTTATGCCTTATGTTGATATACTTTTTGGAAATGAGACAGAAG
721  ---------+---------+---------+---------+---------+---------+ 780
     TCCTTAGTAACTACTTTCAATACGGAATACAACTATATGAAAAACCTTTACTCTGTCTTC

E  S  L  M  K  V  M  P  Y  V  D  I  L  F  G  N  E  T  E  A -

CTGCCACTTTTGCTAGAGAGCAAGGCTTTGAGACTAAAGACATTAAAGAGATAGCCAAAA
781  ---------+---------+---------+---------+---------+---------+ 840
     GACGGTGAAAACGATCTCTCGTTCCGAAACTCTGATTTCTGTAATTTCTCTATCGGTTTT

A  T  F  A  R  E  Q  G  F  E  T  K  D  I  K  E  I  A  K  K -

AGACACAAGCCCTGCCAAAGATGAACTCAAAGAGGCAGCGAATCGTGATCTTCACCCAAG
841  ---------+---------+---------+---------+---------+---------+ 900
     TCTGTGTTCGGGACGGTTTCTACTTGAGTTTCTCCGTCGCTTAGCACTAGAAGTGGGTTC

T  Q  A  L  P  K  M  N  S  K  R  Q  R  I  V  I  F  T  Q  G -

GGAGAGATGACACTATAATGGCTACAGAAAGTGAAGTCACTGCTTTTGCTGTCTTGGATC
901  ---------+---------+---------+---------+---------+---------+ 960
     CCTCTCTACTGTGATATTACCGATGTCTTTCACTTCAGTGACGAAAACGACAGAACCTAG

R  D  D  T  I  M  A  T  E  S  E  V  T  A  F  A  V  L  D  Q -

AAGACCAGAAAGAAATTATTGATACCAATGGAGCTGGAGATGCATTTGTTGGAGGTTTTC
961  ---------+---------+---------+---------+---------+---------+ 1020
     TTCTGGTCTTTCTTTAATAACTATGGTTACCTCGACCTCTACGTAAACAACCTCCAAAAG

D  Q  K  E  I  I  D  T  N  G  A  G  D  A  F  V  G  G  F  L -

TGTCTCAACTGGTCTCTGACAAGCCTCTGACTGAATGTATCCGTGCTGGCCACTATGCAG
1021 ---------+---------+---------+---------+---------+---------+ 1080
     ACAGAGTTGACCAGAGACTGTTCGGAGACTGACTTACATAGGCACGACCGGTGATACGTC

S  Q  L  V  S  D  K  P  L  T  E  C  I  R  A  G  H  Y  A  A -

CAAGCATCATAATTAGACGGACTGGCTGCACCTTTCCTGAGAAGCCAGACTTCCACTGAT
1081 ---------+---------+---------+---------+---------+---------+ 1140
     GTTCGTAGTATTAATCTGCCTGACCGACGTGGAAAGGACTCTTCGGTCTGAAGGTGACTA

S  I  I  I  R  R  T  G  C  T  F  P  E  K  P  D  F  H  *   (SEQ ID NO:8)

GGAAGAGCTGAAAACACAAGCCCAGGAGTCAGACACACCCC     (SEQ ID NO:7)
1141 ---------+---------+---------+---------+- 1181
     CCTTCTCGACTTTTGTGTTCGGGTCCTCAGTCTGTGTGGGG     (SEQ ID NO:9)
```

Fig. 4b

| | | | | | | | |
|---|---|---|---|---|---|---|---|
| SHORT | 1 | .......... | .......MTS | VRENILFGMG | NPLLDISAVV | DKDFLDKYSL | 33 |
| LONG | 1 | MAAAEEEPKP | KKLKVEAPQA | LRENILFGMG | NPLLDISAVV | DKDFLDKYSL | 50 |
| RAT | 1 | .MAAADEPKP | KKLKVEAPEA | LSENVLFGMG | NPLLDISAVV | DKDFLDKYSL | 49 |
| | | | | | | | |
| SHORT | 34 | KPNDQILAED | KHKELFDELV | KKFKVEYHAG | GSTQNSIKVA | QWMIQQPHKA | 83 |
| LONG | 51 | KPNDQILAED | KHKELFDELV | KKFKVEYHAG | GSTQNSIKVA | QWMIQQPHKA | 100 |
| RAT | 50 | KPNDQILAED | KHKELFDELV | KKFKVEYHAG | GSTQNSMKVA | QWMIQEPHRA | 99 |
| | | | | | | | |
| SHORT | 84 | ATFFGCIGID | KFGEILKRKA | AEAHVDAHYY | EQNEQPTGTC | AACITGDNRS | 133 |
| LONG | 101 | ATFFGCIGID | KFGEILKRKA | AEAHVDAHYY | EQNEQPTGTC | AACITGDNRS | 150 |
| RAT | 100 | ATFFGCIGID | KFGEILKSKA | ADAHVDAHYY | EQNEQPTGTC- | AACITGGNRS | 149 |
| | | | | | | | |
| SHORT | 134 | LIANLAAANC | YKKEKHLDLE | KNWMLVEKAR | VCYIAGFFLT | VSPESVLKVA | 183 |
| LONG | 151 | LIANLAAANC | YKKEKHLDLE | KNWMLVEKAR | VCYIAGFFLT | VSPESVLKVA | 200 |
| RAT | 150 | LVANLAAANC | YKKEKHLDLE | NNWMLVEKAR | VYYIAGFFLT | VSPESVLKVA | 199 |
| | | | | | | | |
| SHORT | 184 | HHASENNRIF | TLNLSAPFIS | QFYKESLMKV | MPYVDILFGN | ETEAATFARE | 233 |
| LONG | 201 | HHASENNRIF | TLNLSAPFIS | QFYKESLMKV | MPYVDILFGN | ETEAATFARE | 250 |
| RAT | 200 | RYAAENNRTF | TLNLSAPFIS | QFFKEALMEV | MPYVDILFGN | ETEAATFARE | 249 |
| | | | | | | | |
| SHORT | 234 | QGFETKDIKE | IAKKTQALPK | MNSKRQRIVI | FTQGRDDTIM | ATESEVTAFA | 283 |
| LONG | 251 | QGFETKDIKE | IAKKTQALPK | MNSKRQRIVI | FTQGRDDTIM | ATESEVTAFA | 300 |
| RAT | 250 | QGFETKDIKE | IARKTQALPK | VNSKRQRTVI | FTQGRDDTIV | ATGNDVTAFP | 299 |
| | | | | | | | |
| SHORT | 284 | VLDQDQKEII | DTNGAGDAFV | GGFLSQLVSD | KPLTECIRAG | HYAASIIIRR | 333 |
| LONG | 301 | VLDQDQKEII | DTNGAGDAFV | GGFLSQLVSD | KPLTECIRAG | HYAASIIIRR | 350 |
| RAT | 300 | VLDQNQEEIV | DTNGAGDAFV | GGFLSQLVSN | KPLTECIRAG | HYAASVIIRR | 349 |
| | | | | | | | |
| SHORT | 334 | TGCTFPEKPD | FH | 345 | (SEQ ID NO:5) | | |
| LONG | 351 | TGCTFPEKPD | FH | 362 | (SEQ ID NO:8) | | |
| RAT | 350 | TGCTFPEKPN | FH | 361 | (SEQ ID NO:2) | | |

Fig. 5

| SEQ ID NO | INTERNAL DESIGNATION | SEQUENCE | | | | | | | | |
|---|---|---|---|---|---|---|---|---|---|---|
| PEPTIDES | | | | | | | | | | |
| 10 | PEPTIDE 1 | KTQALPKVNSKR | | | | | | | | |
| 11 | PEPTIDE 2 | KEKVXYHAGGSTQNSMKVAQXMIQXP | | | | | | | | |
| 12 | PEPTIDE 3 | AATFFGHIGIDKFGEILKSKAADAHVDA | | | | | | | | |
| 13 | PEPTIDE 4 | TFTLNLXAPFIXQFEKEAL | | | | | | | | |
| 14 | PEPTIDE 5 | AGHYAASVIIR | | | | | | | | |
| DEGENERATE OLIGOS | | | | | | | | | | |
| 15 | PEPTIDE FRAG 2 | | K | F | K | V | X | Y | H | A |
| 16 | DEGEN OLIGO 2 | 5' AA(G/A) TT(C/T) AA(G/A) GTI III TA(C/T) CA(C/T) GC | | | | | | | | |
| 17 | PEPTIDE FRAG 4 | | Q | F | F | K | E | A | | |
| 18 | DEGEN OLIGO 4 | 3' GC(C/T) TC(C/T) TT(G/A) AA(G/A) AA(T/C) TG | | | | | | | | |

Fig. 6a

| | PCR PRIMERS | |
|---|---|---|
| 20 | OUTER FWD PR | 5'-GAATTCGTGGAGCCAAACCGCGG |
| 21 | INNER FWD PR | 5'-AGAGTCAAGATGGCAGCTGCGG |
| 22 | OUTER REV PR | 5'-GTCTCTGCAGTCTCCACTCC |
| 23 | INNER REV PR | 5'-GCCTGAGTTGCTTTTCTTCCG |
| 24 | OUTER FWD RACE PR | 5'-AATGATGCTGCTTTGTGTGG |
| 25 | INNER FWD RACE PR | 5'-TTGAATCATCCACTGAGCCA |
| 26 | OUTER FWD LONG PR | 5'-GTGGATGGCAGAGGTGGGCTG |
| 27 | INNER FWD LONG PR | 5'-GCCAAAGTGGGGTGGGAGCGCG |
| 28 | OUTER FWD SHORT PR | 5'-GCCGGGAAGCAGTTGCTGTGG |
| 29 | INNER FWD SHORT PR | 5'-GCTGCTGCCCGAGCGGACGTAG |
| 30 | OUTER REV PRIMER | 5'-GGGGTGTCTGCACTCCTGGG |
| 31 | INNER REV PRIMER | 5'-CTTGTGTTTTCAGCTCTTCC |
| 32 | NDEL (SHORT) | 5'-GTAACCTGCCATGGCTCATATGACGTCAGTCAGAGAAATATTC |
| 33 | NDEL (LONG) | 5'-GGGGTGGGAGCGCGCATATGGCGCTGCTGCTGAGGAGGAG |
| 34 | | 5'-AGTTCTACAACGAATCATTG |

Fig. 6b

```
  1  KFKVGYHAGG STONSMKVAO WMIOEPHRAA TFFGC*IGIDK FGEILKSKAA
            PEPTIDE 2                              PEPTIDE 3

51  DAHVDAHYYE QNEQPTGTCA ACITGGNRSL VANLAAANCY XKEXHLDLEN

101  NWMLVEKARV YYIAGFFLTV SPESVLKVAR YAAENNRTFT LNP*SAPFISQ
                                                  PEPTIDE 4

151  FFKE    (SEQ ID NO:19)
```

*= DISCREPANCIES BETWEEN
TRANSLATED DNA AND PEPTIDE
SEQUENCE.

Fig. 8

ADENOSINE KINASE POLYPEPTIDES

CROSS REFERENCE TO RELATED APPLICATIONS

This application is related to the following applications, which are incorporated herein by reference: U.S. patent application Ser. No. (unassigned), entitled "Adenosine Kinase Polynucleotides" by Cowart, Halbert, Kerwin and McNally, Docket No. 5749.US.01 and U.S. patent application Ser. No. (unassigned), entitled "Heterocyclic Substituted Cyclopentane Compounds" by Cowart and Bhagwat, Docket No. 5748.US.01.

TECHNICAL FIELD OF THE INVENTION

The field of this invention is adenosine kinase. More particularly, the field of the present invention is recombinant mammalian adenosine kinase, polynucleotides encoding that adenosine kinase, and methods of making recombinant adenosine kinase.

BACKGROUND OF THE INVENTION

Adenosine kinase (ATP:adenosine 5'-phosphotransferase, EC 2.7.1.20) is a ubiquitous enzyme which catalyzes the phosphorylation of adenosine to AMP, using ATP, preferentially, as the phosphate source. Magnesium is also required for the reaction, and the true cosubstrate is probably the $MgATP^{2-}$ complex (Palella et al., *J. Biol. Chem.* 1980, 255: 5264–5269). Adenosine kinase has broad tissue and species distribution, and has been isolated from yeast (Leibach et al., Hoppe-Seyler's *Z. Physiol. Chem.* 1971, 352: 328–344), a variety of mammalian sources (e.g. Miller et al., *J. Biol. Chem.* 1979, 254: 2339–2345; Palella et al., *J. Biol. Chem.* 1980, 255: 5264–5269; Yamada et al., *Comp. Biochem. Physiol.* 1982, 71B: 367–372; Rottlan and Miras-Portugal, *Eur. J. Biochem.*, 1985, 151: 365–371) and certain microorganisms (e.g. Lobelle-Rich and Reeves, *Am. J. Trop. Med. Hyg.* 1983, 32: 976–979; Datta et al., *J. Biol. Chem.* 1987, 262: 5515–5521). It has been found to be present in virtually every human tissue assayed including kidney, liver, brain, spleen, placenta and pancreas (Andres and Fox, *J. Biol. Chem.* 1979, 254: 11388–11393).

Adenosine kinase is a key enzyme in the control of the cellular concentrations of adenosine (Arch and Newsholme, *Essays Biochem.* 1978, 14: 82–123). Adenosine is a purine nucleoside that is an intermediate in the pathways of purine nucleotide degradation and salvage. In addition, adenosine has many important physiologic effects, many of which are mediated through the activation of specific ectocellular receptors, termed $P_1$ receptors (Bumstock, in *Cell Membrane Receptors for Drugs and Horinones*, 1978, (Bolis and Straub, eds) Raven, N.Y. pp. 107–118; Fredholm et al., *Pharmacol. Rev.* 1994, 46: 143–156). In the central nervous system, adenosine inhibits the release of certain neurotransmiters (Corradetti et al., *Eur. J. Pharmacol.* 1984, 104: 19–26), stabilizes membrane potential (Rudolphi et al., *Cerebrovasc. Brain Metab. Rev.* 1992, 4: 346–360), functions as an endogenous anticonvulsant (Dragunow, *Trends Pharmacol. Sci.* 1986, 7: 128–130) and may have a role as an endogenous neuroprotective agent (Rudolphi et al., *Trends Pharmacol. Sci.* 1992, 13: 439–445). Adenosine has also been implicated in modulating transmission in pain pathways in the spinal cord (Sawynok et al., *Br. J. Pharmacol.* 1986, 88: 923–930), and in mediating the analgesic effects of morphine (Sweeney et al., *J. Pharmacol. Exp. Ther.* 1987, 243: 657–665). In the immune system, adenosine inhibits certain neutrophil functions and exhibits anti-inflammatory effects (Cronstein, *J. Appl. Physiol.* 1994, 76: 5–13).

Adenosine also exerts a variety of effects on the cardiovascular system, including vasodilation, impairment of atrioventricular conduction and endogenous cardioprotection in myocardial ischemia and reperfusion (Mullane and Williams, in *Adenosine and Adenosine Receptors* 1990 (Williams, ed) Humana Press, New Jersey, pp. 289–334). The widespread actions of adenosine also include effects on the renal, respiratory, gastrointestinal and reproductive systems, as well as on blood cells and adipocytes.

Endogenous adenosine release appears to have a role as a natural defense mechanism in various pathophysiologic conditions, including cerebral and myocardial ischemia, seizures, pain, inflammation and sepsis. While adenosine is normally present at low levels in the extracellular space, its release is locally enhanced at the site(s) of excessive cellular activity, trauma or metabolic stress. Once in the extracellular space, adenosine activates specific extracellular receptors to elicit a variety of responses which tend to restore cellular function towards normal (Bruns, *Nucleosides Nucleotides*, 1991, 10: 931–943; Miller and Hsu, *J. Neurotrauma*, 1992, 9: S563–S577). Adenosine has a half-life measured in seconds in extracellular fluids (Moser et al., *Am. J. Physiol.* 1989, 25: C799–C806), and its endogenous actions are therefore highly localized.

The inhibition of adenosine kinase can result in augmentation of the local adenosine concentrations at foci of tissue injury, further enhancing cytoprotection. This effect is likely to be most pronounced at tissue sites where trauma results in increased adenosine production, thereby minimizing systemic toxicities. Pharmacologic compounds directed towards adenosine kinase inhibition provide potential effective new therapies for disorders benefited by the site- and event-specific potentiation of adenosine.

Adenosine kinase is also responsible for the activation of many pharmacologically active nucleosides (Miller et al., *J. Biol. Chem.* 1979, 254: 2339–2345), including tubercidin, formycin, ribavirin, pyrazofurin and 6-(methylmercapto) purine riboside. These purine nucleoside analogs represent an important group of antimetabolites which possess cytotoxic, anticancer and antiviral properties. They serve as substrates for adenosine kinase and are phosphorylated by the enzyme to generate the active form. The loss of adenosine kinase activity has been implicated as a mechanism of cellular resistance to the pharmacologic effects of these nucleoside analogs (e.g. Bennett et al., *Mol. Pharmacol.*, 1966, 2: 432–443; Caldwell et al., *Can. J. Biochem.*, 1967, 45: 735–744; Suttle et al., *Europ. J. Cancer*, 1981, 17: 43–51). Decreased cellular levels of adenosine kinase have also been associated with resistance to the toxic effects of 2'-deoxyadenosine (Hershfield and Kredich, *Proc. Natl. Acad. Sci. USA*, 1980, 77: 4292–4296). The accumulation of deoxyadenosine triphosphate (dATP), derived from the phosphorylation of 2'-deoxyadenosine, has been suggested as a toxic mechanism in the immune defect associated with inheritable adenosine deaminase deficiency (Kredich and Hershfield, in *The Metabolic Basis of Inherited Diseases*, 1989 (Scriver et al., eds), McGraw-Hill, New York, pp. 1045–1075).

Alterations in cellular adenosine kinase activity have also been observed in certain disorders. Adenosine kinase activity was found to be decreased, relative to normal liver, in a variety of rat hepatomas, with activity of the enzyme giving a negative correlation with tumor growth rate (Jackson et al., *Br. J. Cancer*, 1978, 37: 701–713). Adenosine kinase activity was also diminished in regenerating liver after partial hepatectomy in experimental animals (Jackson et al., *Br. J. Cancer*, 1978,37: 701–713). Erythrocyte adenosine kinase activity was found to be diminished in patients with gout (Nishizawa et al., *Clin. Chim. Acta* 1976, 67: 15–20). Lymphocyte adenosine kinase activity was decreased in patients infected with the human immunodeficiency virus (HIV) exhibiting symptoms of AIDS, and increased in asymptomatic HIV-seropositive and HIV-seronegative high-risk subjects, compared to normal healthy controls (Renouf et al., *Clin. Chem.* 1989, 35: 1478–1481). It has been suggested that measurement of adenosine kinase activity may prove useful in monitoring the clinical progress of patients with HIV infection (Renouf et al., *Clin. Chem.* 1989, 35: 1478–1481).

BRIEF SUMMARY OF THE INVENTION

In one aspect, the present invention provides an isolated and purified polynucleotide comprising a nucleotide sequence consisting essentially of a nucleotide sequence selected from the group consisting of (a) the sequence of SEQ ID NO:1 from about nucleotide position 16 to about nucleotide position 1098, the sequence of SEQ ID NO:4 from about nucleotide position 94 to about nucleotide position 1128, or the sequence of SEQ ID NO: 7 from about nucleotide position 51 to about nucleotide position 1136; (b) sequences that are complementary to the sequences of (a), and (c) sequences that, when expressed, encode a polypeptide encoded by a sequence of (a). A preferred polynucleotide is a DNA molecule. In another embodiment, the polynucleotide is an RNA molecule. A preferred polynucleotide is SEQ ID NO: 1, 4 or 7.

In another embodiment, a DNA molecule of the present invention is contained in an expression vector. The expression vector preferably further comprises an enhancer-promoter operatively linked to the polynucleotide. In an especially preferred embodiment, the DNA molecule has the nucleotide sequence of SEQ ID NO:1 from about nucleotide position 16 to about nucleotide position 1098, the sequence of SEQ ID NO:4 from about nucleotide position 94 to about nucleotide position 1128, or the sequence of SEQ ID NO:7 from about nucleotide position 51 to about nucleotide position 1136.

In another aspect, the present invention provides an oligonucleotide of from about 15 to about 50 nucleotides containing a nucleotide sequence of at least 15 nucleotides that is identical or complementary to a contiguous sequence of a polynucleotide of this invention. A preferred oligonucleotide is an antisense oligonucleotide that is complementary to a portion of the polynucleotide of SEQ ID NO: 1,4or7.

The present invention also provides a pharmaceutical composition comprising an antisense oligonucleotide of this invention and a physiologically acceptable diluent.

In another aspect, the present invention provides an adenosine kinase of mammalian origin. In one embodiment, that adenosine kinase is an isolated and purified polypeptide of about 365 or less amino acid residues and comprising the amino acid residue sequence of at least one of:

a) from residue position 7 to residue position 18 of SEQ ID NO: 8;
b) from residue position 26 to residue position 86 of SEQ ID NO: 8;
c) from residue position 100 to residue position 117 of SEQ ID NO: 8;
d) from residue position 122 to residue position 146 of SEQ ID NO: 8;
e) from residue position 153 to residue position 170 of SEQ ID NO: 8;
f) from residue position 172 to residue position 181 of SEQ ID NO: 8;
g) from residue position 183 to residue position 200 of SEQ ID NO: 8;
h) from residue position 210 to residue position 222 of SEQ ID NO: 8;
i) from residue position 230 to residue position 262 of SEQ ID NO: 8;
j) from residue position 279 to residue position 289 of SEQ ID NO: 8;
k) from residue position 311 to residue position 329 of SEQ ID NO: 8;
l) from residue position 331 to residue position 345 of SEQ ID NO: 8; and
m) from residue position 347 to residue position 359 of SEQ ID NO: 8.

Preferably, an adenosine kinase of the present invention has the amino acid residue sequence of SEQ ID NO:2, 5 or 8. More preferably, an adenosine kinase of the present invention is a recombinant human adenosine kinase. A preferred human adenosine kinase has about 365 or less amino acid residues and comprises the amino acid residue sequence of from residue 5 to residue 345 of SEQ ID NO: 5.

In another aspect, the present invention provides two forms of human adenosine kinase designated herein as human short form (SEQ ID NO: 5) and human long form (SEQ ID NO: 8)

In another aspect, the present invention provides a process of making adenosine kinase comprising transforming a host cell with an expression vector that comprises a polynucleotide of the present invention, maintaining the transformed cell for a period of time sufficient for expression of the adenosine kinase and recovering the adenosine kinase. Preferably, the host cell is an eukaryotic host cell such as a mammalian cell, or a bacterial cell. An especially preferred host cell is an *E. coli*. The present invention also provides an adenosine kinase made by a process of this invention. A preferred such adenosine kinase is recombinant human adenosine kinase.

The present invention still further provides for a host cell transformed with a polynucleotide or expression vector of this invention. Preferably, the host cell is a bacterial cell such as an *E. coli*.

BRIEF DESCRIPTION OF THE DRAWINGS

In the drawings which form a portion of the specification:

FIGS. 2a and 2b show a full length clone of rat brain adenosine kinase with deduced amino acid residue sequence.

FIGS. 3a and 3b show a clone of human placenta short form adenosine kinase with deduced amino acid residue sequence.

FIGS. 4a and 4b show a clone of human placenta long form adenosine kinase with deduced amino acid residue sequence.

FIG. 5 shows a comparison of the amino acid residue sequences of short form human placental adenosine kinase, long form human placental adenosine kinase and rat brain adenosine kinase.

FIG. 6 shows various peptide fragments and oligonucleotide sequences used in the isolation and purification of adenosine kinase DNA and polypeptide.

FIG. 8 shows the amino acid residue sequence of a partial clone of rat brain adenosine kinase.

DETAILED DESCRIPTION OF THE INVENTION

I. THE INVENTION

Figure 1:
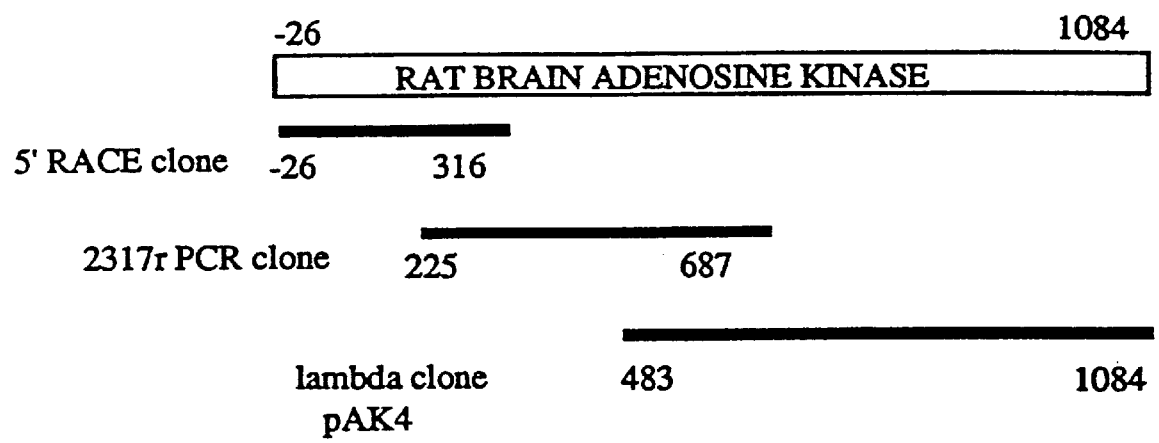
FIG. 1 shows a schematic drawing of clones used to isolate and sequence rat brain adenosine kinase.

The present invention provides isolated and purified polynucleotides that encode adenosine kinase of mammalian origin, expression vectors containing those polynucleotides, host cells transformed with those expression vectors, a process of making adenosine kinase using those polynucleotides and vectors, and isolated and purified adenosine kinase.

II. ADENOSINE KINASE POLYNUCLEOTIDES

In one aspect, the present invention provides an isolated and purified polynucleotide that encodes an adenosine kinase polypeptide of mammalian origin.

A polynucleotide of the present invention that encodes adenosine kinase is an isolated and purified polynucleotide that comprises a nucleotide sequence consisting essentially of a nucleotide sequence selected from the group consisting of (a) the sequence of SEQ ID NO:1 from about nucleotide position 16 to about nucleotide position 1098, the sequence of SEQ ID NO:4 from about nucleotide position 94 to about nucleotide position 1128, or the sequence of SEQ ID NO: 7 from about nucleotide position 51 to about nucleotide position 1136; (b) sequences that are complementary to the sequences of (a), and (c) sequences that, when expressed, encode a polypeptide encoded by the sequences of (a). A preferred polynucleotide is a DNA molecule. In another embodiment, the polynucleotide is an RNA molecule.

The nucleotide sequences and deduced amino acid residue sequences of rat and human adenosine kinase are set forth in FIGS. 2a, 2b, 3a, 3b, 4a and 4b. The nucleotide sequence of SEQ ID NO:1 in FIGS. 2a and 2b is a full length DNA clone of rat brain adenosine kinase. SEQ ID NO:2 in FIGS. 2a and 2b is the deduced amino acid residue sequence of that clone. SEQ ID NO:3 is a complementary DNA strand to SEQ ID NO:1. The nucleotide sequence of SEQ ID NO:4 in FIGS. 3a and 3b is a DNA clone of human short form adenosine kinase. SEQ ID NO:5 in FIGS. 3a and 3b is the deduced amino acid residue sequence of that DNA. SEQ ID NO:6 in FIGS. 3a and 3b is the complementary strand to SEQ ID NO:4. The nucleotide sequence of SEQ ID NO:7 in FIGS. 4a and 4b is a DNA clone of human long form adenosine kinase. SEQ ID NO:8 in FIGS. 4a and 4b is the deduced amino acid residue sequence of that DNA. SEQ ID NO:9 in FIGS. 4a and 4b is the complementary strand to SEQ ID NO:7.

The present invention also contemplates DNA sequences which hybridize under stringent hybridization conditions to the DNA sequences set forth above. Stringent hybridization conditions are well known in the art and define a degree of sequence identity greater than about 70%–80%. The present invention also contemplates naturally occurring allelic variations and mutations of the DNA sequences set forth above so long as those variations and mutations code, on expression, for an adenosine kinase of this invention as set forth hereinafter.

As set forth above, SEQ ID NOs: 1, 4 and 7 are full length cDNA clones of rodent and human adenosine kinase. As is well known in the art, because of the degeneracy of the genetic code, there are numerous other DNA and RNA molecules that can code for the same polypeptides as those encoded by SEQ ID NOs.: 1, 4 and 7. The present invention, therefore, contemplates those other DNA and RNA molecules which, on expression, encode for the polypeptide encoded by SEQ ID NO: 1, 4 or 7. Having identified the amino acid residue sequence of adenosine kinase, and with knowledge of all triplet codons for each particular amino acid residue, it is possible to describe all such encoding RNA and DNA sequences. DNA and RNA molecules other than those specifically disclosed herein and, which molecules are characterized simply by a change in a codon for a particular amino acid are within the scope of this invention.

A Table of codons representing particular amino acids is set forth below in Table 1.

TABLE 1

| First position (5' end) | Second Position | | | | Third position (3' end) |
|---|---|---|---|---|---|
| | T/U | C | A | G | |
| T/U | Phe | Ser | Tyr | Cys | T/U |
| | Phe | Ser | Tyr | Cys | C |
| | Leu | Ser | Stop | Stop | A |
| | Leu | Ser | Stop | Trp | G |
| C | Leu | Pro | His | Arg | T/U |
| | Leu | Pro | His | Arg | C |
| | Leu | Pro | Gln | Arg | A |
| | Leu | Pro | Gln | Arg | G |
| A | Ile | Thr | Asn | Ser | T/U |
| | Ile | Thr | Asn | Ser | C |
| | Ile | Thr | Lys | Arg | A |
| | Met | Thr | Lys | Arg | G |
| G | Val | Ala | Asp | Gly | T/U |
| | Val | Ala | Asp | Gly | C |
| | Val | Ala | Glu | Gly | A |
| | Val | Ala | Glu | Gly | G |

A simple change in a codon for the same amino acid residue within a polynucleotide will not change the structure of the encoded polypeptide. By way of example, it can be seen from SEQ ID NO: 4 (see FIGS. 3a and 3b) that a TCA codon for serine exists at nucleotide positions 100–102 and again at 298–300. It can also be seen from that same sequence, however, that serine can be encoded by a TCT codon (see e.g., nucleotide positions 1015–1017). Substitution of the latter TCT codon for serine with the TCA codon for serine, or visa versa, does not substantially alter the DNA sequence of SEQ ID NO: 4 and results in expression of the same polypeptide. In a similar manner, substitutions of codons for other amino acid residues can be made in a like manner without departing from the true scope of the present invention.

A polynucleotide of the present invention can also be an RNA molecule. A RNA molecule contemplated by the present invention is complementary to or hybridizes under stringent conditions to any of the DNA sequences set forth above. As is well known in the art, such a RNA molecule is characterized by the base uracil in place of thymidine. Exemplary and preferred RNA molecules are mRNA molecules that encode an adenosine kinase of this invention.

The present invention also contemplates oligonucleotides from about 15 to about 50 nucleotides in length, which oligonucleotides serve as primers and hybridization probes for the screening of DNA libraries and the identification of DNA or RNA molecules that encode adenosine kinase. Such primers and probes are characterized in that they will hybridize to polynucleotide sequences encoding adenosine kinase. An oligonucleotide probe or primer contains a nucleotide sequence of at least 15 nucleotides that is identical to or complementary to a contiguous sequence of an adenosine kinase polynucleotide of the present invention. Thus, where an oligonucleotide probe is 25 nucleotides in length, at least 15 of those nucleotides are identical or complementary to a sequence of contiguous nucleotides of an adenosine kinase polynucleotide of the present invention. Exemplary adenosine kinase polynucleotides of the present invention are set forth above.

A preferred oligonucleotde is an antisense oligonucleotide. The present invention provides a synthetic antisense oligonucleotide of less than about 50 nucleotides, preferably less than about 35 nucleotides, more preferably less than about 25 nucleotides and most preferably less than about 20 nucleotides. An antisense oligonucleotide of the present invention is directed against a DNA or RNA molecule that encodes adenosine kinase. Preferably, the antisense oligonucleotide is directed against the protein translational initiation site or the transcriptional start site.

In accordance with this preferred embodiment, an antisense molecule is directed against a region of SEQ. ID NO: 1 from about nucleotide position 1 to about nucleotide position 40; a portion of SEQ. ID NO: 4 from about nucleotide position 80 to about nucleotide position 120 and a portion of SEQ. ID NO: 7 from about nucleotide position 35 to about nucleotide position 75. It is understood by one of ordinary skill in the art that antisense oligonucleotide can be directed either against a DNA or RNA sequence that encodes a specific targel Thus, an antisense oligonucleotide of the present invention can also be directed against polynucleotides that are complementary to those shown in SEQ. ID NOs: 1, 4, and 7 (i.e., SEQ. ID NOs: 3, 6 and 9) as well as the equivalent RNA molecules.

Preferably, the nucleotides of an antisense oligonucleotides are linked by pseudophosphate bonds that are resistant to clevage by exonuclease or endonuclease enzymes. Preferably the pseudophosphate bonds are phosphorothioate bonds. By replacing a phosphodiester bond with one that is resistent to the action of exo-and/or endonuclease, the stability of the nucleic acid in the presence of those enzymes is increased. As used herein, pseudophosphate bonds include, but are not limited to, methylphosphonate, phosphomorpholidate, phosphorothioate, phosphorodithioate and phosphoroselenoate bonds.

An oligonucleotide primer or probe, as well as an antisense oligonucleotide of the present invention can be prepared using standard procedures well known in the art. A preferred method of polynucleotide synthesis is via cyanoethyl phosphoramidite chemistry. A detailed description of the preparation, isolation and purification of polynucleotides encoding mammalian adenosine kinase is set forth below.

A. Rat Adenosine Kinase a. Purification of adenosine kinase

Adenosine kinase was purified from rat brain tissue. Rats were anaesthetized with carbon dioxide, decapitated, and the brain removed and stored at −80° C. prior to use. 350 g of brain tissue was thawed by warming to 4° C. and homogenized in 10 mM Tris (hydroxymethyl) amino methane hydrochloride (Tris-HCl) pH 7.5, 1 mM dithiothreitol (DTT), 0.1 mM ethylenediaminetetraaceticacid (EDTA), 10 $\mu$M Pepstatin (Sigma, St. Louis, Mo.), 10 $\mu$M Leupeptin (Sigma, St. Louis, Mo.) and 10 $\mu$M Chymostatin (Sigma, St Louis, Mo.). Solids were removed by centrifugation at 10,000 g for 1 hour, followed by ultra centrifugation at 100,000 g for 30 minutes. Adenosine kinase was further purified by passing the cleared supernatant over 20 mls of AMP-sepharose (Sigma, SL Louis, Mo.) continuously overnight at 4° C. in TKM buffer (20 mM Tris-HCl pH 7.0, 150 mM KCl, 20 mM $MgCl_2$ 1 mM DTT, 1 mM EDTA). The column was then washed successively with two column volumes each of TKM with 500 mM NaCl, TKM with 10 mM adenosine triphosphate (ATP), TKM with 5 mM adenosine and TKM with 1.3 mM nicotinamide adenine dinucleotide phosphate, reduced (NADPH). Adenosine kinase activity eluted with the adenosine wash. Based on initial activity, 86% of material was recovered at this step, which gave a 1,270 fold purification and a specific activity of 0.77 U/mg (one U is defined as the amount of enzyme required to phosphorylate 1 $\mu$mol of adenosine per minute at 37° C., at pH 7.5). Samples containing significant adenosine kinase activity were pooled and concentrated in a Centricon 100™ (Amicon Inc. Beverly, Mass.). The concentrate was then applied to a 1 ml Q-Sepharose ™ FPLC column (Pharmacia, Piscataway, N.J.). The column was equilibrated and the protein loaded in 10 mM Tris pH 7.5, 0.4 mM DTT. Adenosine kinase was eluted with a gradient of KCl from 0 to 100 mM in the same buffer, with the adenosine kinase activity eluting as a major peak at approximately 50 mM KCl. The protein was a single homogeneous band by SDS PAGE using a precast 12.5% acrylamide gel (Daiichi Pure Chemicals Company, Tokyo, Japan) and stained with the Biorad silver stain kit (Biorad, Richmond, Calif.). The overall purification of adenosine kinase from cytosol was 21,700 fold, with a final specific activity of 13 U/mg.

b. Digestion of adenosine kinase with endoproteinase ARG C

20 $\mu$g of purified adenosine kinase in 200 $\mu$l of 10 mM Tris pH 7.5, 100 mM KCl, 0.1 mM DTT was concentrated to 100 $\mu$l under vacuum. The protein solution was adjusted to 20 mM ethanol amine and 4M urea. 20 $\mu$l of 50 mM DTT and 5 mM EDTA were added and reduction was carried out for 30 mins at room temperature under $N_2$, 80 $\mu$l of 100 mM Tris-HCl, pH 7.6, 10 mM $CaCl_2$ were then added. 1.2 $\mu$g of Endo Arg C (Boehringer Mannheim, Indianapolis, Ind.) was then added and digestion carried out for 20 hours at 37° C. under $N_2$. The activity was quenched with the addition of 20 $\mu$l 10% Trifluoroacetic acid (TFA)/5% Acetonitrile ($CH_3CN$).

c. Reverse phase high pressure liquid chromatography (RP-HPLC) of the adenosine kinase Endo Arg C digest The Endo Arg C digest of adenosine kinase was separated by RP-HPLC using a 1×100 mm ABI-OD300 column (Applied Biosystems, Foster City, Calif.) and Pharmacia SMART™ chromatography system (Pharmacia, Pitscataway, N.J.). The starting buffer was 0.1% TFA/5% $CH_3CN$. The elution buffer was 0.082% TFA/80% $CH_3CN$. A flow rate of 200 $\mu$l/min. was used. After loading the digest onto the column, chromatography was accomplished by running a 55 minute gradient from 0 to 100% of the eluting buffer. Fractions were collected using the SMART™ system's peak detection capabilities and stored at −80° C. prior to analysis.

d. Peptide sequencing

Peptide fragments were sequenced by sequential Edman degradation on an Applied Biosystems 476™ or 477™ (Applied Biosystems, Foster City, Calif.) sequencer following manufacturer's recommended protocols. Data were collected and analyzed on a Perkin Elmer Nelson A/D941 (Perkin Elmer, Norwalk, Conn.) The sequences of 5 different peptide fragments were determined. The sequences of those fragments are shown in FIG. 6 and designated SEQ ID NOs:10–14 where X at position 5 in SEQ ID NO: 11 indicates an indefinite residue. X at positions 21 and 25 in SEQ ID NO: 11 and at positions 7 and 12 in SEQ ID NO:13 indicate indeterminate residues.

Sequencing of the purified protein without proteolytic cleavage was attempted unsuccessfully, suggesting that the amino terminus of the protein may be blocked.

e. Design of oligonucleotides

Degenerate oligonucleotides were designed using the peptide sequences SEQ ID NOs:10–14. The less discriminating base Inosine (I) was substituted in regions of ambiguity and high degeneracy. Note that the parentheses in nucleotide sequence indicate an equal mix of two nucleotides to account for ambiguity in codon usage. A variety of degenerate primers were synthesized and tested. The primer pair which resulted in the formation of a bona fide PCR product is shown in FIG. 6 and designated SEQ ID NOs:16 and 18. The portions of peptide SEQ ID NOs:11 and 13 used to design the probes are shown in FIG. 6 as sequences SEQ ID NOs:15 and 17. The sequences shown as SEQ ID NOs:15 and 17 represent portions of SEQ ID NOs:11 and 13, respectively.

f. Cloning of adenosine kinase from rat brain

Rat brain messenger RNA (mRNA) was purchased (Clontech, Palo Alto, Calif.). One μg was reverse transcribed into cDNA using the Moloney Murine Leukemia Virus Reverse Transcriptase (Stratagene, La Jolla, Calif.) following the manufacturer's recommended protocol. At the end of the reaction, cDNA was precipitated with ethanol and stored in 20 μl sterile distilled water. 1 μl was used for each Polymerase Chain Reaction (PCR) (Saiki, R. K., Gelfand, D. H., Stoffel, S., Scharf, S. J., Higuchi, R., Horn, G. T., Mullis,K. B., Ehrlich, H. A., (1988) *Science* 239 487–91). The PCR was carried out in a Perkin Elmer 9600™ Thermal Cycler. The reaction mix contained 1 μl cDNA, 20 pmol of each of SEQ ID NOs:16 and 18 in FIG. 6, 0.2 mM deoxynucleotide triphosphates (dNTPs), 10 μl 10×PCR buffer (200 mM Tris-HCl, pH 8.4, 500 mM KCl), 10 μl 50 mM $MgCl_2$ and $H_2O$ to 100 μl. Directly following incubation for 2 minutes at 94° C. to denature template DNA, 5 units of Taq polymerase (BRL, Gaithersburg, Md.) were added to each reaction. The reaction was taken through 25 cycles, each cycle comprising 94° C.-30 seconds, 50° C.-60 seconds, and 72° C.-60 seconds.

Following the last cycle, the reactions were incubated a further 5 minutes at 72° C. then stored at 4° C. prior to gel analysis. For gel analysis, reactions were precipitated with 0.1 vol. 5M NaCl and 2 vols. ice cold 100% ethanol. Samples were incubated at −20° C. for at least 1 hour and centrifuged at 4° C. for 1 hour in a microfuge. One half of the reaction was visualized by UV light following electrophoresis on a 1% agarose gel containing 0.1 μg/ml ethidium bromide, revealing a predominant band in the region of 500 bp in size. The remainder of the reaction was cloned into the vector pGEM-T™ (Promega, Madison, Wis.), following the manufacturer's recommended protocols. 7 μl of insert DNA was mixed with 1 μl ligase buffer (250 mM Tris-HCl pH 7.6, 50 mM KCl, 25 mM $MgCl_2$ 5 mM ATP, 5 mM DTT, 25% w/v polyethylene glycol 8000), 1 μl of vector and 1 unit T4 DNA ligase (Promega, Madison, Wis.). Reactions were incubated at 4° C. overnight.

*E. coli* Maximum Efficiency™ DH5∝(BRL, Gaithersburg, Md.) were transformed with 5 μl of the ligation reaction and then spread on Lennox Broth (LB) agar containing 150 μg/ml Ampicillin (Microdiagnostics, Lombard, Ill.). 50 μl 2% X-Gal (5-bromo4-chloro-3-indolyl-beta-D-galactoside)(Sigma, St. Louis, Mo.) dissolved in dimethylformamide was spread on the plate prior to use. Transformants with insert grew as white colonies on this indicator. Individual colonies were picked into L broth (Gibco-BRL, Gaithersburg, Md.) containing 100 μg/ml ampicillin (sodium salt) (Sigmna, St. Louis, Mo.) and grown overnight at 37° C. with vigorous aeration in LB media (Gibco BRL, Gaithersburg, Md.). Template DNA was prepared from white colonies using Promega Magic™ minipreps (Promega, Madison, Wis.). Insert DNA was sequenced utilizing vector specific primers on an Applied Biosystems 373 DNA sequencer ( ABI, Foster City, Calif.) following the manufacturer's recommended protocols. Sequence analysis was performed using Sequencher™ software. (GeneCodes, Ann Arbor, Mich.).

g. Comparison of peptide and DNA sequence

DNA sequences of inserts were translated in all reading frames and compared to adenosine kinase peptides using the University of Wisconsin Genetics Computer Group sequence analysis package (Genetics ComputerGroup, Madison, Wis.). One clone, designated 2317r was identified as a partial clone of adenosine kinase based on its identity with amino acid sequences of the peptides obtained by ArgC digestion. Translation of this clone in frame 3 is shown in FIG. 8 as SEQ ID NO:19 with identification of the peptide fragments set forth above.

h. Rat brain cDNA library screening

A rat brain cDNA library was screened with the partial adenosine kinase clone 2317r, in an attempt to isolate a full-length clone. Clone 2317r was digested with restriction enzymes Apa1 and Spe1 (BRL, Gaithersburg, Md.) to liberate the insert. Digested DNA was subjected to electrophoresis in 1% low melting point agarose (LMPA) containing 0.1 μg/ml ethidium bromide. The insert band was visualized by UV light then excised with a sterile razor blade. The agarose slice was weighed and water added at 1.5 ml per gram of agarose. The gel slice was heated to 100° C. for 10 mins then equilibrated at 37° C. for 30 mins. The melted agarose was divided into 100 μl aliquots and stored at −20° C. Insert DNA was labeled with $^{32}P$ by random priming using the BRL DNA labeling kit ( Gibco- BRL, Gaithersburg, Md.) using the method of Finberg and Vogelstein for random priming of fragments directly from low melting point agarose gel slices (Finberg, A.P. And Vogelstein, B. (1984) *Anal. Biochem.* 132 (1) 6–13).

Unincorporated $^{32}P$ was removed by spin column chromatography using Quick Spin™ G25-sepharose columns, (Boehringer Mannheim, Indianapolis, Ind.). A rat brain cDNA library in lambda ZAPII was obtained from Stratagene (La Jolla, Calif.). This library was used to infect *E. coli* XL1Blue MRF (Stratagene, La Jolla, Calif.) following the manufacturer's recommended protocols. The library was titrated to yield approximately 5,000 plaques per 10 cm plastic petri dish on NZCYM agar (Becton Dickinson, Cockeysvile, Md.). 40 dishes were prepared in this way (approximately 200,000 plaques). Plaque lifts were taken in duplicate on Duralon-UV™ membrane (Stratagene, La Jolla, Calif.) and fixed by exposure to UV light for 2 minutes. Filters were prehybridized in 50% formamide, 1M NaCl, 10% Dextran Sulphate,1% SDS and 100 μg/ml sheared salmon sperm DNA (Sigma, St. Louis, Mo.) at 42° C. in a volume of 20 mls per 20 filters. Hybridization was carried out at 42° C. in the same buffer with the addition of 5–9×$10^6$ cpm radiolabelled probe. After hybridization, filters were washed 3 times in 0.1×SSC (20×SSC=3M NaCl, 0.3M Na Citrate), 0.1% SDS at 42° C. Filters were air dried and exposed to Kodak X-AR™ film (Eastman Kodak, New Haven, Conn.) at −70° C. and the film developed according to the manufacturer's recommendations.

Clones identified by hybridization signal were plaque purified through multiple cycles of growth and amplification. Plaque purification consisted of removing a region of the agarose plate around the positive plaque (around 5 mm$^2$) and incubating it in 0.5 mls of SM medium (100 mM Tris-HCl, 0.01 mM MgSO$_4$-7H$_2$O, 100 mM NaCl, 0.01% gelatin) to permit phage particles to diffuse from the agar. 5 μl of this diffusate were then used to infect *E. coli* XL1Blue cells as described. Plaque lifts were taken as described previously and filters hybridized with fresh radioactive probe. Enrichment was repeated in this way 3 times until all of the plaques on the plate reacted positively with the probe.

i. Sub cloning of rat brain adenosine kinase lambda clone

The rat brain adenosine kinase insert was copied from the lambda Zap II clone by PCR using vector specific primers (T7 and T3 promoter primers, Stratagene, La Jolla, Calif.) in a PCR reaction mix comprising 10 pmol T3 and T7 primers, 10 μl 10×PCR buffer (Gibco- BRL),10 μl 50 mM MgCl$_2$, 0.2 mM dNTP, 5 μl plaque pure phage suspension in SM buffer, adjusted to 100 μl with sterile distilled water. The PCR conditions were for 30 cycles as follows; 94° C. for 5 minutes to denature DNA followed by 30 cycles of 94° C. for 1 minute, 60° C. for 1 minute and 72° C. for 2 minutes. 0.1 μl of the amplified reaction mix was visualized by UW light following electrophoresis in a 1% agarose gel containing 0.1 μg/ml ethidium bromide. The insert band was approximately 800 bp in length. The insert was sequenced as described above. Sequence analysis indicated that the clone was lacking the 5' end of the mRNA but overlapped the original clone and contained the 3' untranslated region, up to and including the poly A tail (FIG. 1).

j. Isolation of the amino terminal end of the rat adenosine kinase mRNA

5' RACE (Random Amplification of CDNA Ends, Frohman, M. A., Dush, M. K., Martin, G. R. (1988) *Proc. Natl. Acad. Sci. USA* 85 8998–9002, Belyavski, A., Vinogradova, T., Rajewski,K., (1989) *Nucleic Acids Res.* 17 2919–2932) was used to isolate the 5' end of the rat brain adenosine kinase gene. 5' Race Ready™ cDNA from rat brain was obtained from Clontech (Palo Alto, Calif.) This cDNA is optimized by the manufacturer to include the 5' end of all genes expressed in the particular tissue, and includes an "anchor" oligonucleotide ligated to the 5' end of each cDNA. Nested PCR was carried out following the manufacturer's protocols with an anchor-specific promoter and gene specific internal primers. This procedure yielded an intact 5' end for the adenosine kinase gene. The deduced sequence of the complete rat brain adenosine kinase gene was then generated by overlapping contiguous analysis. FIG. 1 illustrates the overlapping clones that were sequenced to generate the full-length coding sequence.

k. Isolation of the full-length rat brain AK

Nested PCR primers were then designed to obtain the full length coding sequence. These primers bound to the 5' and 3' untranslated region of the gene. Those primers are shown in FIG. 6 and designated SEQ ID NOs:20–23.

These primers were used in the PCR to generate a full length rat brain gene from rat brain Quickclone™ cDNA (Clontech, Palo Alto, Calif.). After 1 set of 30 cycles of PCR following conditions detailed above with the outer primers (SEQ ID Nos: 20 and 22 in FIG. 6), the PCR mix was diluted 1 in 10 and the PCR repeated with the inner set of nested primers (SEQ ID Nos: 21 and 23 in FIG. 6). An aliquot of the PCR reaction was visualized by UV light following electrophoresis on a 1% agarose gel containing 0.1 μg/ml ethidium bromide. A homogeneous DNA fragment of about 1 kb was obtained, consistent with the full length rat brain gene. The PCR fragment was then cloned into the vector pGEM-T as described above. Inserts from multiple clones were sequenced as described above, and a consensus sequence for rat brain adenosine kinase was generated. A portion of that consensus sequence as well as the encoding polynucleotide sequences are shown in FIGS. 2a and 2b.

FIGS. 2a and 2b shows the full length consensus sequence of rat brain DNA and the deduced amino acid residue sequence for adenosine kinase. SEQ ID NO:1 in FIGS. 2a and 2b represents the coding strand. SEQ ID NO:2 shows the deduced amino acid residue sequence from that coding strand. SEQ ID NO:3 represents the complementary DNA strand.

l. Sequence comparison of the rat brain adenosine kinase gene

Using the database searching algorithm, BLAST, (Altschul, S. F., Gish, W., Miller, W., Myers,.E. W., Lipman, D. J. (1990) *J. Mol. Biol.* 215:403–410) the DNA and deduced protein sequence of rat brain adenosine kinase was compared to other nucleic acids and proteins in the GENbank and EMBL databases. Limited sequence similarity was found with a class of prokaxyotic sugar kinases. Using the GCG program MOTIFS (GCG sequence analysis software package, program manual v.8 (1994)), which searches for amino acid domains shared among common classes of proteins listed in the Prosite database (Bairoch, A. And Bucker, P. (1994) *Nucleic Acids Res.* 22 3583–89), rat brain adenosine kinase was observed to have a common amino acid motif shared among these prokaryotic sugar kinases (Bork, P., Sander, C., Valencia, A. (1993) *Protein Sci.* 2 31–40). However, rat brain adenosine kinase has no significant sequence homology with other reported nucleoside kinases, and, surprisingly, does not appear to contain a classical ATP binding motif.

B. Human Adenosine Kinase a. Cloning of the human isozymes of AK

The rat brain adenosine kinase cDNA sequence was used as a probe to screen several human cDNA libraries in an effort to clone a homologous human gene. The full length rat brain gene, excluding untranslated regions, was radiolabelled by random priming as described previously. This probe was then used to screen cDNA libraries from human hippocampus, human placenta, human MOLT-4 lymphoid cells and human Raji lymphoid cells (all from Clontech, Palo Alto, Calif.), human skeletal muscle (Stratagene, La Jolla, Calif.). Libraries were plated on either *E. coli* XL-1 blue cells or *E. coli* Y1090 cells, depending upon which lambda strain was used (either lambda Zap II or lambda gt11 respectively). Libraries were plated at a density of 18,000 plaques per plate on 150 mm polystyrene petri dishes in NZCYM medium. Hybridization was carried out as described above. Several hybridization-positive clones were identified from human placental cDNA.

b. Sequence analysis of the human placental putative adenosine kinase clones

Individual lambda phage clones were obtained after three rounds of plaque purification as described above. Inserts were obtained from a plaque purified sample by PCR as described previously, using lambda gt11 specific oligonucleotides. Full-length PCR products were cloned into pGEM-T and sequenced as described previously. That full length clone is shown in FIGS. 3a and 3b. In FIGS. 3a and 3b, the coding DNA strand is shown as SEQ ID NO:4 with the deduced amino acid residue sequence shown as SEQ ID:5. The complementary DNA sequence is shown as SEQ ID NO:6.

Comparison of the amino acid sequence of the human placental cDNA clone to that of rat brain revealed some major differences at the amino terminus as shown in FIG. 5. In FIG. 5, the full length rat brain adenosine kinase sequence is shown as SEQ ID NO:2. The amino acid residue sequence of the human form of adenosine kinase, designated herein as the short form, is shown as SEQ ID NO:5.

It can be calculated from FIG. 5 that the identity between human short form and rat enzyme is 86% at the amino acid level. However, there are significant differences at the amino terminus. In order to verify these differences, 5' RACE was performed as described above on human brain 5' RACE Ready™ cDNA (Clontech, Palo Alto, Calif.). Oligonucleotides used are shown in FIG. 6 and designated as SEQ ID NOs:24–25. A major band was visualized by UV light following gel electrophoresis and ethidium bromide staining of the PCR. PCR products were cloned into pGEM-T (Promega, Madison, Wis.) and white colonies were sequenced as described above. Two forms of adenosine kinase, which differ at their amino termini, were identified by this procedure. Nested PCR from cDNA using oligonucleotides SEQ ID NOs:26–31 specific for human adenosine kinase was used to obtain full length clones of both forms of adenosine kinase. Full length PCR products were cloned into pGEMT and sequenced as described above. Sequence analysis of these full length clones reveals that they are identical except at their 5' termini. The full length clone of the long form of human adenosine kinase is shown in FIGS. 4a and 4b. In FIGS. 4a and 4b, the coding DNA strand is shown as SEQ ID NO:7 with the deduced amino acid residue sequence shown as SEQ ID:8. The complementary DNA sequence is shown as SEQ ID NO:9.

III. ADENOSINE KINASE POLYPEPTIDES

In another aspect, the present invention provides an adenosine kinase of mammalian origin. An adenosine kinase of the present invention is a polypeptide of about 365 or less amino acid residues. As set forth above, forms of adenosine kinase have been identified with from 345 to 362 amino acid residues. The various forms of adenosine kinase are characterized by a high degree of sequence identity. By way of example, the identity between human short form and rat enzyme is 86% at the amino acid level.

As set forth above, when the amino acid residue sequence of adenosine kinase was compared against other known amino acid residue sequences using a database searching algorithm, only very limited sequence similarity was found with a class of prokaryotic sugar kinases. Although rat adenosine kinase was found to have a common amino acid motif shared among prokaryotic sugar kinases, rat brain adenosine kinase had no significant sequence homology with other reported nucleoside kinases.

The high degree of identity amongst various forms of herein described adenosine kinase, when combined with the absence of identity to other reported nucleoside kinases allows for definition of the adenosine kinase amino acid residue sequence by the regions of residue identity. Thus, in one embodiment, an adenosine kinase is an isolated and purified polypeptide of about 365 or less amino acid residues, having adenosine kinase biological activity and comprising at least one of the following amino acid residue sequences:

a) from residue position 7 to residue position 18 of SEQ ID NO: 8;

b) from residue position 26 to residue position 86 of SEQ ID NO: 8;

c) from residue position 100 to residue position 117 of SEQ ID NO: 8;

d) from residue position 122 to residue position 146 of SEQ ID NO: 8;

e) from residue position 153 to residue position 170 of SEQ ID NO: 8;

f) from residue position 172 to residue position 181 of SEQ ID NO: 8;

g) from residue position 183 to residue position 200 of SEQ ID NO: 8;

h) from residue position 210 to residue position 222 of SEQ ID NO: 8;

i) from residue position 230 to residue position 262 of SEQ ID NO: 8;

j) from residue position 279 to residue position 289 of SEQ ID NO: 8;

k) from residue position 311 to residue position 329 of SEQ ID NO: 8;

l) from residue position 331 to residue position 345 of SEQ ID NO: 8; and m) from residue position 347 to residue position 359 of SEQ ID NO: 8.

More preferably, an adenosine kinase of the present invention comprises two or more of the above sequences. Most preferably, an adenosine kinase has all of the above sequences.

Preferably, an adenosine kinase of the present invention has the amino acid residue sequence of any of SEQ ID NO:2, 5, or 8.

More preferably, an adenosine kinase is a recombinant human adenosine kinase. Human forms of adenosine kinase are shown in SEQ ID NOs:5 and 8. SEQ ID NO:5 represents a short form of human adenosine kinase. SEQ ID NO:8 represents a second, long form of human adenosine kinase. It can be seen from an examination of those sequences that all human forms share a high degree of sequence identity. Thus, human adenosine kinase can be defined as a polypeptide of about 365 or less amino acid residues comprising the amino acid residue sequence of from residue position 5 to residue position 345 of SEQ ID NO: 5. A preferred recombinant human adenosine kinase has the amino acid residue sequence of SEQ ID NO: 5 or 8.

The present invention also contemplates amino acid residue sequences that are substantially duplicative of the sequences set forth herein such that those sequences demonstrate like biological activity to disclosed sequences. Such contemplated sequences include those sequences characterized by a minimal change in amino acid residue sequence or type (e.g., conservatively substituted sequences) which insubstantial change does not alter the basic nature and biological activity of adenosine kinase.

It is well known in the art that modifications and changes can be made in the structure of a polypeptide without substantially altering the biological function of that peptide. For example, certain amino acids can be substituted for other amino acids in a given polypeptide without any appreciable loss of function. In making such changes, substitutions of like amino acid residues can be made on the basis of relative similarity of side-chain substituents, for example, their size, charge, hydrophobicity, hydrophilicity, and the like.

As detailed in U.S. Pat. No. 4,554,101, incorporated herein by reference, the following hydrophilicity values have been assigned to amino acid residues: Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4). It is understood that an amino acid residue can be substituted for another having a similar hydrophilicity value (e.g., within a value of plus or minus 2.0) and still obtain a biologically equivalent polypeptide.

In a similar manner, substitutions can be made on the basis of similarity in hydropathic index. Each amino acid residue has been assigned a hydropathic index on the basis of its hydrophobicity and charge characteristics. Those hydropathic index values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). In making a substitution based on the hydropathic index, a value of within plus or minus 2.0 is preferred.

An adenosine kinase polypeptide of the present invention has numerous uses. By way of example, such a polypeptide can be used in a screening assay for the identification of drugs or compounds that inhibit the action of adenosine kinase (e.g., agonist and antagonist). As set forth above, adenosine kinase is an enzyme that catalizes the phosphorolation of adenosine to AMP. A screening assay for the identification of inhibitors of adenosine kinase, therefore, can be established whereby the ability of an inhibitor to inhibit the action of adenosine kinase can be determined by exposing adenosine in the presence of necessary cofactors to a polypeptide of the present invention and varying amounts of compounds suspected of inhibiting the activity of adenosine kinase.

In addition, an adenosine kinase polypeptide of the present invention can be used to produce antibodies that immunoreact specifically with adenosine kinase. Means for producing antibodies are well known in the art An antibody directed against adenosine kinase can be a polyclonal or a monoclonal antibody.

Antibodies against adenosine kinase can be prepared by immunizing an animal with an adenosine kinase polypeptide of the present invention. Means for immunizing animals for the production of antibodies are well known in the art By way of an example, a mammal can be injected with an inoculum that includes a polypeptide as described herein above. The polypeptide can be included in an inoculum alone or conjugated to a carrier protein such as keyhole limpet hemocyanin (KLH). The polypeptide can be suspended, as is well known in the art, in an adjuvant to enhance the immunogenicity of the polypeptide. Sera containing immunologically active antibodies are then produced from the blood of such immunized animals using standard procedures well known in the art.

The identification of antibodies that immunoreact specifically with adenosine kinase is made by exposing sera suspected of containing such antibodies to a polypeptide of the present invention to form a conjugate between antibodies and the polypeptide. The existence of the conjugate is then determined using standard procedures well known in the art.

An adenosine kinase polypeptide of the present invention can also be used to prepare monoclonal antibodies against adenosine kinase and used as a screening assay to identify such monoclonal antibodies. Monoclonal antibodies are produced from hybridomas prepared in accordance with standard techniques such as that described by Kohler et al. (*Nature*, 256:495, 1975). Briefly, a suitable mammal (e.g., BALB/c mouse) is immunized by injection with a polypeptide of the present invention. After a predetermined period of time, splenocytes are removed from the mouse and suspended in a cell culture medium. The splenocytes are then fused with an immortal cell line to form a hybridoma. The formed hyridomas are grown in cell culture and screened for their ability to produce a monoclonal antibody against adenosine kinase. Screening of the cell culture medium is made with a polypeptide of the present invention.

IV. METHOD OF MAKING ADENOSINE KINASE

In another aspect, the present invention provides a process of making adenosine kinase. In accordance with that process, a suitable host cell is transformed with a polynucleotide of the present invention. The transformed cell is maintained for a period of time sufficient for expression of the adenosine kinase. The formed adenosine kinase is then recovered.

Means for transforming host cells in a manner such that those cells produce recombinant polypeptides are well known in the art. Briefly, a polynucleotide that encodes the desired polypeptide is placed into an expression vector suitable for a given host cell. That vector can be a viral vector, phage or plasmid. In a preferred embodiment, a host cell used to produce adenosine kinase is an eukaryotic host cell and an expression vector is an eukaryotic expression vector (i.e., a vector capable of directing expression in a eukaryotic cell). Such eukaryotic expression vectors are well known in the art.

In another preferred embodiment, the host cell is a bacterial cell. An especially preferred bacterial cell is an *E. coli*. Thus, a preferred expression vector is a vector capable of directing expression in *E. coli*.

A polynucleotide of an expression vector of the present invention is preferably operatively associated or linked with an enhancer-promoter. A promoter is a region of a DNA molecule typically within about 100 nucleotide pairs in front of (upstream of) the point at which transcription begins. That region typically contains several types of DNA sequence elements that are located in similar relative positions in different genes. As used herein, the term "promoter" includes what is referred to in the art as an upstream promoter region or a promoter of a generalized RNA polymerase transcription unit.

Another type of transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from a transcription start site so long as the promoter is present.

As used herein, the phrase "enhancer-promoter" means a composite unit that contains both enhancer and promoter elements. An enhancer promoter is operatively linked to a coding sequence that encodes at least one gene product As used herein, the phrase "operatively linked" or its gramatical equivalent means that a regulatory sequence element (e.g. an enhancer-promoter or transcription terminating region) is connected to a coding sequence in such a way that the transcription of that coding sequence is controlled and regulated by that enhancer-promoter. Means for operatively linking an enhancer-promoter to a coding sequence are well known in the art.

An enhancer-promoter used in an expression vector of the present invention can be any enhancer-promoter that drives expression in a host cell. By employing an enhancer-promoter with well known properties, the level of expression can be optimized For example, selection of an enhancer-promoter that is active in specifically transformed cells permits tissue or cell specific expression of the desired product. Still further, selection of an enhancer-promoter that is regulated in response to a specific physiological signal can permit inducible expression.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA). Enhancer-promoters and transcription-terminating regions are well known in the art The selection of a particular enhancer-promoter or transcription-terminating region will depend, as is also well known in the art, on the cell to be transformed.

A clone of the short form of adenosine kinase was identified by DNA sequence analysis to be identical to the consensus described previously. This clone was used in all subsequent expression studies. Adenosine kinase was expressed in *E. coli* BL21(DE3)(Novagen, Madison, Wis.) under the control of the T7 promoter. An Nde I site was engineered onto the adenosine kinase gene by PCR cloning into the expression construct with the oligonucleotide SEQ ID NO:32, shown in FIG. 6.

This oligonucleotide, when paired with a 3' outer oligonucleotide for PCR as described above using SEQ ID NO: 30, yielded a single PCR product which comprised the adenosine kinase gene with the newly engineered enzyme site. The product was digested with the restriction enzyme Hha I to cleave all of the parent plasmid but leave the insert intact.

PCR products were cloned into pGEM-T (Promega, Madison, Wis.). Positive clones were grown up in quantity and plasmid DNA purified by Qiagen™ midi-prep (Qiagen, Chatsworth, Calif.). Purified DNA was cut with Nde I and Sal I and the reaction was electrophoresed on a 1% agarose gel containing 0.1 μg/ml ethidium bormide. The gel region containing the adenosine kinase insert was visualized by UV light and then excised with a sterile razor blade. The insert was purified out of the gel slice by extrusion through a 0.2 micron filter. The parent plasmid pET21 a was also digested with Nde I and Sal I and purified by Chromospin™ column chromatography.(Clontech, Palo Alto, Calif.). Ligations were performed using the Takara DNA ligation kit (Panvera, Madison, Wis.). Reactions were carried out at 16° C. overnight with 2 μl pET 21A (Nde 1 and Sal1 cut), 4 μl insert, 24 μl buffer A, and 6 μl buffer B. 5 μl of the ligation mix was transformed into Maximum Efficiency DH5α as described above. Colonies were screened by the PCR, using a T7 terminator primer and an adenosine kinase internal primer (SEQ ID NO: 34 of FIG. 6). 15 of 20 colonies yielded PCR fragments corresponding in size to that expected for the adenosine kinase cDNA. Two of these colonies were expanded by overnight growth in LB media, their DNA prepared and transformed into *E. coli* strains BL21(DE3) and HMS 174(DE3), the strains used for pET vector expression. Individual transformants were picked, grown to an OD of 0.6 in 100 mls Superbroth™ and then induced with 0.4 mM isopropyl-β-thiogalactopyranoside (IPTG). Cultures were grown for a further 2 hours to allow optimal expression of insert DNA.

Cells were harvested by centrifugation and lysed by french pressure cell. Lysates were spun in a microfuge to separate soluble cytosolic material from insoluble components. SDS polyacrylamide gel analysis of these separated fractions revealed a significant protein band at 40 KDa associated with the insoluble component suggesting that the recombinant protein formed inclusion bodies. A protein of 40 KDa molecular weight was present in the samples containing adenosine kinase inserts, consistent with the expected size of adenosine kinase.

In the same way, the long form of human adenosine kinase was expressed using the oligonucleotide in SEQ ID NO: 33 to PCR the gene. All other conditions were the same as set forth above.

The expression vector containing the encoding DNA sequence for short form human adenosine kinase is designated pET21AK5 (short) and the expression vector containing the encoding DNA sequence for long form human adenosine kinase is designated pET21AK18 (long). Both vectors were deposited, under the terms of the Budapest Treaty, on Jun. 5, 1995 in the American Type Culture Collection, 12301 Parklawn Drive, Rockville, Md. 20852, and have been assigned ATCC Accession Nos: 97194 (pET21AK5) and 97195(pET21AK18).

Figure 7:
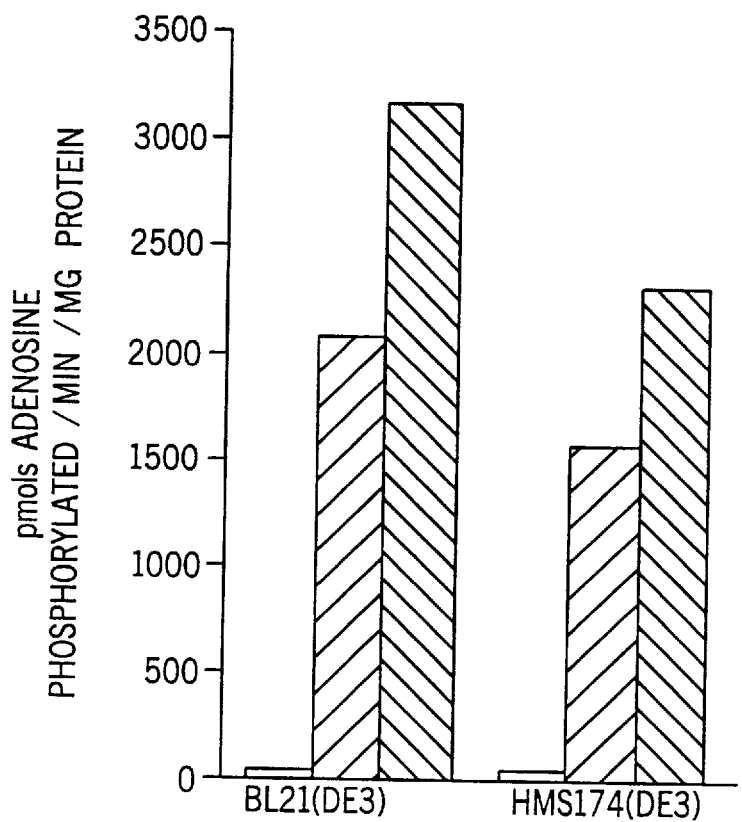
FIG. 7 shows the specific activity of adenosine kinase from two independent clones of transformed *E. coli*. BL21 and HMS represent two different *E. coli* strains and the vertical bars represent the specific activity of two different AK clones.

Adenosine kinase activity of cell supernatants was assayed radiometrically. Assays were carried out at ambient temperature in a final volume of 100 μl. The reaction mixture contained 64 mM Tris HCl (pH 7.5), 0.2 mM MgCl2, 1 mM ATP, 0.2 μM U [$^{14}$C]-adenosine (542 mCi/mmol, Amersham) and appropriate volumes of the supernatant sample. The reaction was terminated after 15 min. by spotting 40 μl of the reaction mixture onto disks of Whatman DE-81 anion exchange paper. DE-81 disks were then air-dried, washed for 10 min. in 2 mM ammonium formate, rinsed successively with distilled water, methanol and acetone, and dried. DE-81 disks were then soaked for 5 min. in 0. 1N HCl/0.4M KCl before addition of scintillation cocktail and counting by liquid scintillation counting. Specific activities (pmol adenosine phosphorylatedi min./mg protein) for two independent clones are shown in FIG. 7.

The present invention also contemplates a host cell transformed with a polynucleotide or expression vector of this invention. Means for transforming cells and polynucleotides and expression vectors used to transform host cells are set forth above. Preferably, the host cell is an eukaryotic host cell such as a mammalian cell or a prokaryotic cell such as an *E. coli*.

V. PHARMACEUTICAL COMPOSITIONS

The present invention also provides a pharmaceutical composition comprising a polypeptide or a polynucleotide of this invention and a physiologically acceptable diluent.

In a preferred embodiment, the present invention includes one or more antisense oligonucleotides, as set forth above, formulated into compositions together with one or more non-toxic physiologically tolerable or acceptable diluents, carriers, adjuvants or vehicles that are collectively referred to herein as diluents, for parenteral injection, for oral administration in solid or liquid form, for rectal or topical administration, or the like.

The compositions can be administered to humans and animals either orally, rectally, parenterally, intracisternally, intravaginally, intraperitoneally, locally, or as a buccal or nasal spray.

Compositions suitable for parenteral administration can comprise physiologically acceptable sterile aqueous or non-aqueous solutions, dispersions, suspensions or emulsions and sterile powders for reconstitution into such sterile solutions or dispersions. Examples of suitable diluents include water, ethanol, polyols, suitable mixtures thereof, vegetable oils and injectable organic esters such as ethyl oleate. Proper fluidity can be maintained, for example, by the use of a coating such as lecithin, by the maintenance of the required particle size in the case of dispersions and by the use of surfactants.

Compositions can also contain adjuvants such as preserving, wetting, emulsifying, and dispensing agents. Prevention of the action of microorganisms can be insured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form can be brought about by the use of agents delaying absorption, for example, aluminum monostearate and gelatin.

Besides such inert diluents, the composition can also include sweetening, flavoring and perfuming agents. Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonit, agar-agar and tragacanth, or mixtures of these substances, and the like.

SEQUENCE LISTING ( 1 ) GENERAL INFORMATION:

( i i i ) NUMBER OF SEQUENCES: 34

( 2 ) INFORMATION FOR SEQ ID NO: 1:

( i ) SEQUENCE CHARACTERISTICS:
        ( A ) LENGTH: 1190 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 16..1101
        ( C ) IDENTIFICATION METHOD: experimental
        ( D ) OTHER INFORMATION: /evidence=EXPERIMENTAL ( i x ) FEATURE:
        ( A ) NAME/KEY: mat_peptide
        ( B ) LOCATION: 16..1098

( x i ) SEQUENCE DESCRIPTION: SEQ ID NO: 1:

```
GGG  ATT  AGA  GTC  AAG  ATG  GCA  GCT  GCG  GAC  GAG  CCG  AAG  CCC  AAG  AAG        48
                         Met  Ala  Ala  Ala  Asp  Glu  Pro  Lys  Pro  Lys  Lys
                          1                   5                        10

CTC  AAG  GTG  GAA  GCG  CCA  GAA  GCG  CTG  AGT  GAA  AAT  GTG  CTG  TTT  GGA        96
Leu  Lys  Val  Glu  Ala  Pro  Glu  Ala  Leu  Ser  Glu  Asn  Val  Leu  Phe  Gly
               15                        20                        25

ATG  GGG  AAT  CCT  CTT  CTT  GAC  ATC  TCT  GCT  GTG  GTA  GAC  AAA  GAT  TTC       144
Met  Gly  Asn  Pro  Leu  Leu  Asp  Ile  Ser  Ala  Val  Val  Asp  Lys  Asp  Phe
          30                        35                        40

CTT  GAT  AAG  TAT  TCT  CTG  AAA  CCA  AAC  GAC  CAG  ATC  TTG  GCC  GAA  GAC       192
Leu  Asp  Lys  Tyr  Ser  Leu  Lys  Pro  Asn  Asp  Gln  Ile  Leu  Ala  Glu  Asp
     45                        50                        55

AAG  CAC  AAG  GAA  TTG  TTT  GAT  GAA  CTT  GTA  AAA  AAA  TTC  AAA  GTT  GAA       240
Lys  His  Lys  Glu  Leu  Phe  Asp  Glu  Leu  Val  Lys  Lys  Phe  Lys  Val  Glu
60                       65                        70                       75

TAT  CAT  GCC  GGT  GGG  TCC  ACG  CAG  AAT  TCA  ATG  AAA  GTG  GCT  CAG  TGG       288
Tyr  His  Ala  Gly  Gly  Ser  Thr  Gln  Asn  Ser  Met  Lys  Val  Ala  Gln  Trp
                    80                        85                       90

ATG  ATT  CAG  GAG  CCA  CAC  AGA  GCA  GCA  ACG  TTC  TTC  GGA  TGC  ATT  GGG       336
Met  Ile  Gln  Glu  Pro  His  Arg  Ala  Ala  Thr  Phe  Phe  Gly  Cys  Ile  Gly
               95                       100                       105

ATA  GAT  AAG  TTC  GGG  GAG  ATC  CTG  AAG  AGC  AAA  GCC  GCA  GAT  GCA  CAC       384
Ile  Asp  Lys  Phe  Gly  Glu  Ile  Leu  Lys  Ser  Lys  Ala  Ala  Asp  Ala  His
          110                       115                       120

GTG  GAC  GCC  CAT  TAC  TAT  GAG  CAG  AAC  GAG  CAG  CCC  ACA  GGA  ACG  TGC       432
Val  Asp  Ala  His  Tyr  Tyr  Glu  Gln  Asn  Glu  Gln  Pro  Thr  Gly  Thr  Cys
```

-continued

```
              125                          130                             135
GCT  GCA  TGC  ATC  ACC  GGT  GGC  AAC  CGG  TCT  CTT  GTT  GCT  AAC  CTT  GCT         480
Ala  Ala  Cys  Ile  Thr  Gly  Gly  Asn  Arg  Ser  Leu  Val  Ala  Asn  Leu  Ala
140                      145                      150                      155

GCC  GCC  AAT  TGT  TAT  AAG  AAA  GAA  AAG  CAC  CTT  GAT  CTG  GAG  AAC  AAC         528
Ala  Ala  Asn  Cys  Tyr  Lys  Lys  Glu  Lys  His  Leu  Asp  Leu  Glu  Asn  Asn
                    160                      165                      170

TGG  ATG  TTG  GTA  GAG  AAA  GCC  AGA  GTT  TAC  TAC  ATA  GCT  GGC  TTC  TTT         576
Trp  Met  Leu  Val  Glu  Lys  Ala  Arg  Val  Tyr  Tyr  Ile  Ala  Gly  Phe  Phe
               175                      180                      185

CTC  ACC  GTC  TCC  CCA  GAG  TCA  GTG  TTG  AAA  GTG  GCT  CGC  TAT  GCT  GCC         624
Leu  Thr  Val  Ser  Pro  Glu  Ser  Val  Leu  Lys  Val  Ala  Arg  Tyr  Ala  Ala
          190                      195                      200

GAG  AAC  AAC  AGG  ACC  TTC  ACT  CTT  AAC  CTG  TCC  GCA  CCG  TTC  ATT  AGC         672
Glu  Asn  Asn  Arg  Thr  Phe  Thr  Leu  Asn  Leu  Ser  Ala  Pro  Phe  Ile  Ser
     205                      210                      215

CAG  TTC  TTC  AAG  GAA  GCC  TTG  ATG  GAA  GTC  ATG  CCT  TAT  GTT  GAC  ATC         720
Gln  Phe  Phe  Lys  Glu  Ala  Leu  Met  Glu  Val  Met  Pro  Tyr  Val  Asp  Ile
220                      225                      230                      235

CTC  TTT  GGA  AAT  GAG  ACG  GAG  GCT  GCC  ACT  TTT  GCT  AGA  GAG  CAA  GGC         768
Leu  Phe  Gly  Asn  Glu  Thr  Glu  Ala  Ala  Thr  Phe  Ala  Arg  Glu  Gln  Gly
                    240                      245                      250

TTT  GAG  ACT  AAA  GAC  ATT  AAA  GAA  ATA  GCC  AGA  AAG  ACG  CAG  GCT  CTT         816
Phe  Glu  Thr  Lys  Asp  Ile  Lys  Glu  Ile  Ala  Arg  Lys  Thr  Gln  Ala  Leu
               255                      260                      265

CCA  AAG  GTG  AAC  TCG  AAG  AGG  CAG  AGG  ACC  GTG  ATC  TTC  ACC  CAA  GGG         864
Pro  Lys  Val  Asn  Ser  Lys  Arg  Gln  Arg  Thr  Val  Ile  Phe  Thr  Gln  Gly
          270                      275                      280

AGA  GAT  GAC  ACT  ATA  GTA  GCT  ACA  GGA  AAT  GAT  GTC  ACT  GCT  TTC  CCT         912
Arg  Asp  Asp  Thr  Ile  Val  Ala  Thr  Gly  Asn  Asp  Val  Thr  Ala  Phe  Pro
     285                      290                      295

GTC  TTG  GAT  CAA  AAC  CAG  GAA  GAG  ATC  GTT  GAC  ACC  AAT  GGA  GCT  GGA         960
Val  Leu  Asp  Gln  Asn  Gln  Glu  Glu  Ile  Val  Asp  Thr  Asn  Gly  Ala  Gly
300                      305                      310                      315

GAT  GCA  TTT  GTA  GGA  GGG  TTT  CTG  TCT  CAG  CTG  GTC  TCC  AAC  AAG  CCT        1008
Asp  Ala  Phe  Val  Gly  Gly  Phe  Leu  Ser  Gln  Leu  Val  Ser  Asn  Lys  Pro
                    320                      325                      330

CTG  ACT  GAA  TGC  ATC  CGG  GCC  GGG  CAC  TAT  GCA  GCG  AGC  GTC  ATC  ATT        1056
Leu  Thr  Glu  Cys  Ile  Arg  Ala  Gly  His  Tyr  Ala  Ala  Ser  Val  Ile  Ile
               335                      340                      345

AGG  CGA  ACT  GGC  TGT  ACT  TTT  CCT  GAG  AAG  CCA  AAC  TTC  CAC  TGACGGAAGA      1108
Arg  Arg  Thr  Gly  Cys  Thr  Phe  Pro  Glu  Lys  Pro  Asn  Phe  His
          350                      355                      360

AAAGCAACTC  AGGCAATCAC  TAGTGCGGCC  GCCTGCAGGT  CGACCATATG  GGAGAGCTCC              1168

CAACGCGTTG  GATGCATAGC  TT                                                          1190
```

( 2 ) INFORMATION FOR SEQ ID NO: 2:

( i ) SEQUENCE CHARACTERISTICS:
        ( A ) LENGTH: 361 amino acids
        ( B ) TYPE: amino acid
        ( C ) STRANDEDNESS: double
        ( D ) TOPOLOGY: linear ( i i ) MOLECULE TYPE: protein ( x i ) SEQUENCE DESCRIPTION: SEQ ID NO: 2:

```
              Met  Ala  Ala  Ala  Asp  Glu  Pro  Lys  Pro  Lys  Lys
                   1              5                        10

Leu  Lys  Val  Glu  Ala  Pro  Glu  Ala  Leu  Ser  Glu  Asn  Val  Leu  Phe  Gly
               15                      20                      25
```

| | | | | | | | | | | | | | |
|---|---|---|---|---|---|---|---|---|---|---|---|---|---|
| Met | Gly | Asn 30 | Pro | Leu | Leu | Asp | Ile 35 | Ser | Ala | Val | Val | Asp 40 | Lys | Asp | Phe |
| Leu | Asp 45 | Lys | Tyr | Ser | Leu | Lys 50 | Pro | Asn | Asp | Gln | Ile 55 | Leu | Ala | Glu | Asp |
| Lys 60 | His | Lys | Glu | Leu | Phe 65 | Asp | Glu | Leu | Val | Lys 70 | Lys | Phe | Lys | Val | Glu 75 |
| Tyr | His | Ala | Gly | Gly 80 | Ser | Thr | Gln | Asn | Ser 85 | Met | Lys | Val | Ala | Gln 90 | Trp |
| Met | Ile | Gln | Glu 95 | Pro | His | Arg | Ala | Ala 100 | Thr | Phe | Phe | Gly | Cys 105 | Ile | Gly |
| Ile | Asp | Lys 110 | Phe | Gly | Glu | Ile | Leu 115 | Lys | Ser | Lys | Ala | Ala 120 | Asp | Ala | His |
| Val | Asp 125 | Ala | His | Tyr | Tyr | Glu 130 | Gln | Asn | Glu | Gln | Pro 135 | Thr | Gly | Thr | Cys |
| Ala 140 | Ala | Cys | Ile | Thr | Gly 145 | Gly | Asn | Arg | Ser | Leu 150 | Val | Ala | Asn | Leu | Ala 155 |
| Ala | Ala | Asn | Cys | Tyr 160 | Lys | Lys | Glu | Lys | His 165 | Leu | Asp | Leu | Glu | Asn 170 | Asn |
| Trp | Met | Leu | Val 175 | Glu | Lys | Ala | Arg | Val 180 | Tyr | Tyr | Ile | Ala | Gly 185 | Phe | Phe |
| Leu | Thr | Val 190 | Ser | Pro | Glu | Ser | Val 195 | Leu | Lys | Val | Ala | Arg 200 | Tyr | Ala | Ala |
| Glu | Asn 205 | Asn | Arg | Thr | Phe | Thr 210 | Leu | Asn | Leu | Ser | Ala 215 | Pro | Phe | Ile | Ser |
| Gln 220 | Phe | Phe | Lys | Glu | Ala 225 | Leu | Met | Glu | Val | Met 230 | Pro | Tyr | Val | Asp | Ile 235 |
| Leu | Phe | Gly | Asn | Glu 240 | Thr | Glu | Ala | Ala | Thr 245 | Phe | Ala | Arg | Glu | Gln 250 | Gly |
| Phe | Glu | Thr | Lys 255 | Asp | Ile | Lys | Glu | Ile 260 | Ala | Arg | Lys | Thr | Gln 265 | Ala | Leu |
| Pro | Lys | Val 270 | Asn | Ser | Lys | Arg | Gln 275 | Arg | Thr | Val | Ile | Phe 280 | Thr | Gln | Gly |
| Arg | Asp 285 | Asp | Thr | Ile | Val | Ala 290 | Thr | Gly | Asn | Asp | Val 295 | Thr | Ala | Phe | Pro |
| Val 300 | Leu | Asp | Gln | Asn | Gln 305 | Glu | Glu | Ile | Val | Asp 310 | Thr | Asn | Gly | Ala | Gly 315 |
| Asp | Ala | Phe | Val | Gly 320 | Gly | Phe | Leu | Ser | Gln 325 | Leu | Val | Ser | Asn | Lys 330 | Pro |
| Leu | Thr | Glu | Cys 335 | Ile | Arg | Ala | Gly | His 340 | Tyr | Ala | Ala | Ser | Val 345 | Ile | Ile |
| Arg | Arg | Thr 350 | Gly | Cys | Thr | Phe | Pro 355 | Glu | Lys | Pro | Asn | Phe 360 | His | | |

( 2 ) INFORMATION FOR SEQ ID NO: 3:

( i ) SEQUENCE CHARACTERISTICS:
        ( A ) LENGTH: 1190 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 3:

```
AAGCTATGCA TCCAACGCGT TGGGAGCTCT CCCATATGGT CGACCTGCAG GCGGCCGCAC        60
TAGTGATTGC CTGAGTTGCT TTTCTTCCGT CAGTGGAAGT TTGGCTTCTC AGGAAAAGTA       120
```

-continued

| | | | | | |
|---|---|---|---|---|---|
| CAGCCAGTTC | GCCTAATGAT | GACGCTCGCT | GCATAGTGCC | CGGCCCGGAT | GCATTCAGTC | 180 |
| AGAGGCTTGT | TGGAGACCAG | CTGAGACAGA | AACCCTCCTA | CAAATGCATC | TCCAGCTCCA | 240 |
| TTGGTGTCAA | CGATCTCTTC | CTGGTTTTGA | TCCAAGACAG | GGAAAGCAGT | GACATCATTT | 300 |
| CCTGTAGCTA | CTATAGTGTC | ATCTCTCCCT | TGGGTGAAGA | TCACGGTCCT | CTGCCTCTTC | 360 |
| GAGTTCACCT | TTGGAAGAGC | CTGCGTCTTT | CTGGCTATTT | CTTTAATGTC | TTTAGTCTCA | 420 |
| AAGCCTTGCT | CTCTAGCAAA | AGTGGCAGCC | TCCGTCTCAT | TTCCAAGAG | GATGTCAACA | 480 |
| TAAGGCATGA | CTTCCATCAA | GGCTTCCTTG | AAGAACTGGC | TAAGTAACGG | TGCGGACAGG | 540 |
| TTAAGAGTGA | AGGTCCTGTT | GTTCTCGGCA | GCATAGCGAG | CCACTTTCAA | CACTGACTCT | 600 |
| GGGGAGACGG | TGAGAAAGAA | GCCAGCTATG | TAGTAAACTC | TGGCTTTCTC | TACCAACATC | 660 |
| CAGTTGTTCT | CCAGATCAAG | GTGCTCTTCT | TTCTTATAAC | AATTGGCGGC | AGCAAGGTTA | 720 |
| GCAACAAGAG | ACCGGTTGCC | ACCGGTGATG | CATGCAGCGC | ACGTTCCTGT | GGGCTGCTCG | 780 |
| TTCTGCTCAT | AGTAATGGGC | GTCCACGTGT | GCATCTGCGG | CTTTGCTCTT | CAGGATCTCC | 840 |
| CCGAACTCAT | CTATCCCAAT | GCATCCGAAG | AACGTTGCTG | CTCTGTGTGG | CTCCTGAATC | 900 |
| ATCCACTGAG | CCACTTTCAT | TGAATTCTGC | GTGGACCCAC | CGGCATGATA | TTCAACTTTG | 960 |
| AATTTTTTA | CAAGTTCATC | AAACAATTCC | TTGTGCTTGT | CTTCGGCCAA | GATCTGGTCG | 1020 |
| TTTGGTTTCA | GAGAATACTT | ATCAAGGGAA | TCTTTGTCTA | CCACAGCAGA | GATGTCAAGA | 1080 |
| AGAGGATTCC | CCATTCCAAA | CAGCACATTT | TCACTCAGCG | CTTCTGGCGC | TTCCACCTTG | 1140 |
| AGCTTCTTGG | GCTTCGGCTC | GTCCGCAGCT | GCCATCTTGA | CTCTAATCCC | | 1190 |

( 2 ) INFORMATION FOR SEQ ID NO: 4:

( i ) SEQUENCE CHARACTERISTICS:
( A ) LENGTH: 1172 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 94..1131

( i x ) FEATURE:
( A ) NAME/KEY: mat_peptide
( B ) LOCATION: 94..1128

( x i ) SEQUENCE DESCRIPTION: SEQ ID NO: 4:

```
GCCGGGAAGC  AGTTGCTGTG  GTACCTGCTG  CTGCCCGAGC  GGACGTAGAG  CATCGGACGC         60

GGGCGCCGTG  GCGTTGGGCA  GGAGGGCGAA  GCC ATG ACG TCA GTC AGA GAA AAT           114
                                        Met Thr Ser Val Arg Glu Asn
                                         1               5

ATT CTC TTT GGA ATG GGA AAT CCT CTG CTT GAC ATC TCT GCT GTA GTG            162
Ile Leu Phe Gly Met Gly Asn Pro Leu Leu Asp Ile Ser Ala Val Val
         10                  15                  20

GAC AAA GAT TTC CTT GAT AAG TAT TCT CTG AAA CCA AAT GAC CAA ATC           210
Asp Lys Asp Phe Leu Asp Lys Tyr Ser Leu Lys Pro Asn Asp Gln Ile
     25                  30                  35

TTG GCT GAA GAC AAA CAC AAG GAA CTG TTT GAT GAA CTT GTG AAA AAA           258
Leu Ala Glu Asp Lys His Lys Glu Leu Phe Asp Glu Leu Val Lys Lys
 40                 45                  50                  55

TTC AAA GTC GAA TAT CAT GCT GGT GGC TCT ACC CAG AAT TCA ATT AAA           306
Phe Lys Val Glu Tyr His Ala Gly Gly Ser Thr Gln Asn Ser Ile Lys
                 60                  65                  70
```

| | | | | | | | | | | | | | | | | |
|---|---|---|---|---|---|---|---|---|---|---|---|---|---|---|---|---|
| GTG | GCT | CAG | TGG | ATG | ATT | CAA | CAG | CCA | CAC | AAA | GCA | GCA | ACA | TTT | TTT | 354 |
| Val | Ala | Gln | Trp 75 | Met | Ile | Gln | Gln | Pro 80 | His | Lys | Ala | Ala | Thr 85 | Phe | Phe | |
| GGA | TGC | ATT | GGG | ATA | GAT | AAA | TTT | GGG | GAG | ATC | CTG | AAG | AGA | AAA | GCT | 402 |
| Gly | Cys | Ile 90 | Gly | Ile | Asp | Lys | Phe 95 | Gly | Glu | Ile | Leu | Lys | Arg 100 | Lys | Ala | |
| GCT | GAA | GCC | CAT | GTG | GAT | GCT | CAT | TAC | TAC | GAG | CAG | AAT | GAG | CAG | CCA | 450 |
| Ala | Glu 105 | Ala | His | Val | Asp | Ala | His 110 | Tyr | Tyr | Glu | Gln | Asn 115 | Glu | Gln | Pro | |
| ACA | GGA | ACT | TGT | GCT | GCA | TGC | ATC | ACT | GGT | GAC | AAC | AGG | TCC | CTC | ATA | 498 |
| Thr 120 | Gly | Thr | Cys | Ala | Ala 125 | Cys | Ile | Thr | Gly | Asp 130 | Asn | Arg | Ser | Leu | Ile 135 | |
| GCT | AAT | CTT | GCT | GCT | GCC | AAT | TGT | TAT | AAA | AAG | GAA | AAA | CAT | CTT | GAT | 546 |
| Ala | Asn | Leu | Ala | Ala 140 | Ala | Asn | Cys | Tyr | Lys 145 | Lys | Glu | Lys | His | Leu 150 | Asp | |
| CTG | GAG | AAA | AAC | TGG | ATG | TTG | GTA | GAA | AAA | GCA | AGA | GTT | TGT | TAT | ATA | 594 |
| Leu | Glu | Lys | Asn 155 | Trp | Met | Leu | Val | Glu | Lys 160 | Ala | Arg | Val | Cys 165 | Tyr | Ile | |
| GCA | GGC | TTT | TTT | CTT | ACA | GTT | TCC | CCA | GAG | TCA | GTA | TTA | AAG | GTG | GCT | 642 |
| Ala | Gly | Phe 170 | Phe | Leu | Thr | Val | Ser 175 | Pro | Glu | Ser | Val | Leu 180 | Lys | Val | Ala | |
| CAC | CAT | GCT | TCT | GAA | AAC | AAC | AGG | ATT | TTC | ACT | TTG | AAT | CTA | TCT | GCA | 690 |
| His | His 185 | Ala | Ser | Glu | Asn | Asn 190 | Arg | Ile | Phe | Thr | Leu 195 | Asn | Leu | Ser | Ala | |
| CCG | TTT | ATT | AGC | CAG | TTC | TAC | AAG | GAA | TCA | TTG | ATG | AAA | GTT | ATG | CCT | 738 |
| Pro 200 | Phe | Ile | Ser | Gln | Phe 205 | Tyr | Lys | Glu | Ser | Leu 210 | Met | Lys | Val | Met | Pro 215 | |
| TAT | GTT | GAT | ATA | CTT | TTT | GGA | AAT | GAG | ACA | GAA | GCT | GCC | ACT | TTT | GCT | 786 |
| Tyr | Val | Asp | Ile | Leu 220 | Phe | Gly | Asn | Glu | Thr 225 | Glu | Ala | Ala | Thr | Phe 230 | Ala | |
| AGA | GAG | CAA | GGC | TTT | GAG | ACT | AAA | GAC | ATT | AAA | GAG | ATA | GCC | AAA | AAG | 834 |
| Arg | Glu | Gln | Gly 235 | Phe | Glu | Thr | Lys | Asp 240 | Ile | Lys | Glu | Ile | Ala 245 | Lys | Lys | |
| ACA | CAA | GCC | CTG | CCA | AAG | ATG | AAC | TCA | AAG | AGG | CAG | CGA | ATC | GTG | ATC | 882 |
| Thr | Gln | Ala 250 | Leu | Pro | Lys | Met | Asn 255 | Ser | Lys | Arg | Gln | Arg 260 | Ile | Val | Ile | |
| TTC | ACC | CAA | GGG | AGA | GAT | GAC | ACT | ATA | ATG | GCT | ACA | GAA | AGT | GAA | GTC | 930 |
| Phe | Thr 265 | Gln | Gly | Arg | Asp | Asp 270 | Thr | Ile | Met | Ala | Thr 275 | Glu | Ser | Glu | Val | |
| ACT | GCT | TTT | GCT | GTC | TTG | GAT | CAA | GAC | CAG | AAA | GAA | ATT | ATT | GAT | ACC | 978 |
| Thr 280 | Ala | Phe | Ala | Val | Leu 285 | Asp | Gln | Asp | Gln | Lys 290 | Glu | Ile | Ile | Asp | Thr 295 | |
| AAT | GGA | GCT | GGA | GAT | GCA | TTT | GTT | GGA | GGT | TTT | CTG | TCT | CAA | CTG | GTC | 1026 |
| Asn | Gly | Ala | Gly | Asp 300 | Ala | Phe | Val | Gly | Gly 305 | Phe | Leu | Ser | Gln | Leu 310 | Val | |
| TCT | GAC | AAG | CCT | CTG | ACT | GAA | TGT | ATC | CGT | GCT | GGC | CAC | TAT | GCA | GCA | 1074 |
| Ser | Asp | Lys | Pro 315 | Leu | Thr | Glu | Cys | Ile 320 | Arg | Ala | Gly | His | Tyr 325 | Ala | Ala | |
| AGC | ATC | ATA | ATT | AGA | CGG | ACT | GGC | TGC | ACC | TTT | CCT | GAG | AAG | CCA | GAC | 1122 |
| Ser | Ile | Ile 330 | Ile | Arg | Arg | Thr | Gly 335 | Cys | Thr | Phe | Pro | Glu 340 | Lys | Pro | Asp | |
| TTC | CAC | TGA | TGGAAGAGCT | | GAAAACACAA | | GCCCAGGAGT | | | GCAGACACCCC | | | | | | 1172 |
| Phe | His 345 | * | | | | | | | | | | | | | | |

( 2 ) INFORMATION FOR SEQ ID NO: 5:

( i ) SEQUENCE CHARACTERISTICS:
        ( A ) LENGTH: 345 amino acids
        ( B ) TYPE: amino acid
        ( D ) TOPOLOGY: linear (ii) MOLECULE TYPE: protein (xi) SEQUENCE DESCRIPTION: SEQ ID NO: 5:

| Met 1 | Thr | Ser | Val | Arg 5 | Glu | Asn | Ile | Leu | Phe 10 | Gly | Met | Gly | Asn | Pro 15 | Leu |
|---|---|---|---|---|---|---|---|---|---|---|---|---|---|---|---|
| Leu | Asp | Ile | Ser 20 | Ala | Val | Val | Asp 25 | Lys | Asp | Phe | Leu | Asp 30 | Lys | Tyr | Ser |
| Leu | Lys | Pro 35 | Asn | Asp | Gln | Ile | Leu 40 | Ala | Glu | Asp | Lys | His 45 | Lys | Glu | Leu |
| Phe | Asp 50 | Glu | Leu | Val | Lys | Lys 55 | Phe | Lys | Val | Glu | Tyr 60 | His | Ala | Gly | Gly |
| Ser 65 | Thr | Gln | Asn | Ser | Ile 70 | Lys | Val | Ala | Gln | Trp 75 | Met | Ile | Gln | Gln | Pro 80 |
| His | Lys | Ala | Ala | Thr 85 | Phe | Phe | Gly | Cys | Ile 90 | Gly | Ile | Asp | Lys | Phe 95 | Gly |
| Glu | Ile | Leu | Lys 100 | Arg | Lys | Ala | Ala | Glu 105 | Ala | His | Val | Asp | Ala 110 | His | Tyr |
| Tyr | Glu | Gln 115 | Asn | Glu | Gln | Pro | Thr 120 | Gly | Thr | Cys | Ala | Ala 125 | Cys | Ile | Thr |
| Gly | Asp 130 | Asn | Arg | Ser | Leu | Ile 135 | Ala | Asn | Leu | Ala | Ala 140 | Ala | Asn | Cys | Tyr |
| Lys 145 | Lys | Glu | Lys | His | Leu 150 | Asp | Leu | Glu | Lys | Asn 155 | Trp | Met | Leu | Val | Glu 160 |
| Lys | Ala | Arg | Val | Cys 165 | Tyr | Ile | Ala | Gly | Phe 170 | Phe | Leu | Thr | Val | Ser 175 | Pro |
| Glu | Ser | Val | Leu 180 | Lys | Val | Ala | His | His 185 | Ala | Ser | Glu | Asn | Asn 190 | Arg | Ile |
| Phe | Thr | Leu 195 | Asn | Leu | Ser | Ala | Pro 200 | Phe | Ile | Ser | Gln | Phe 205 | Tyr | Lys | Glu |
| Ser | Leu 210 | Met | Lys | Val | Met | Pro 215 | Tyr | Val | Asp | Ile | Leu 220 | Phe | Gly | Asn | Glu |
| Thr 225 | Glu | Ala | Ala | Thr | Phe 230 | Ala | Arg | Glu | Gln | Gly 235 | Phe | Glu | Thr | Lys | Asp 240 |
| Ile | Lys | Glu | Ile | Ala 245 | Lys | Lys | Thr | Gln | Ala 250 | Leu | Pro | Lys | Met | Asn 255 | Ser |
| Lys | Arg | Gln | Arg 260 | Ile | Val | Ile | Phe | Thr 265 | Gln | Gly | Arg | Asp | Asp 270 | Thr | Ile |
| Met | Ala | Thr 275 | Glu | Ser | Glu | Val | Thr 280 | Ala | Phe | Ala | Val | Leu 285 | Asp | Gln | Asp |
| Gln | Lys 290 | Glu | Ile | Ile | Asp | Thr 295 | Asn | Gly | Ala | Gly | Asp 300 | Ala | Phe | Val | Gly |
| Gly 305 | Phe | Leu | Ser | Gln | Leu 310 | Val | Ser | Asp | Lys | Pro 315 | Leu | Thr | Glu | Cys | Ile 320 |
| Arg | Ala | Gly | His | Tyr 325 | Ala | Ala | Ser | Ile | Ile 330 | Ile | Arg | Arg | Thr | Gly 335 | Cys |
| Thr | Phe | Pro | Glu 340 | Lys | Pro | Asp | Phe | His | | | | | | | |

(2) INFORMATION FOR SEQ ID NO: 6:

(i) SEQUENCE CHARACTERISTICS:
        (A) LENGTH: 1172 base pairs
        (B) TYPE: nucleic acid
        (C) STRANDEDNESS: double
        (D) TOPOLOGY: linear (ii) MOLECULE TYPE: DNA (genomic)

( x i ) SEQUENCE DESCRIPTION: SEQ ID NO: 6:

| | | | | | |
|---|---|---|---|---|---|
| GGGGTGTCTG | CACTCCTGGG | CTTGTGTTTT | CAGCTCTTCC | ATCAGTGGAA | GTCTGGCTTC | 60
| TCAGGAAAGG | TGCAGCCAGT | CCGTCTAATT | ATGATGCTTG | CTGCATAGTG | GCCAGCACGG | 120
| ATACATTCAG | TCAGAGGCTT | GTCAGAGACC | AGTTGAGACA | GAAAACCTCC | AACAAATGCA | 180
| TCTCCAGCTC | CATTGGTATC | AATAATTTCT | TTCTGGTCTT | GATCCAAGAC | AGCAAAAGCA | 240
| GTGACTTCAC | TTTCTGTAGC | CATTATAGTG | TCATCTCTCC | CTTGGGTGAA | GATCACGATT | 300
| CGCTGCCTCT | TTGAGTTCAT | CTTTGGCAGG | GCTTGTGTCT | TTTTGGCTAT | CTCTTTAATG | 360
| TCTTTAGTCT | CAAAGCCTTG | CTCTCTAGCA | AAAGTGGCAG | CTTCTGTCTC | ATTTCCAAAA | 420
| AGTATATCAA | CATAAGGCAT | AACTTTCATC | AATGATTCCT | TGTAGAACTG | GCTAATAAAC | 480
| GGTGCAGATA | GATTCAAAGT | GAAAATCCTG | TTGTTTTCAG | AAGCATGGTG | AGCCACCTTT | 540
| AATACTGACT | CTGGGGAAAC | TGTAAGAAAA | AAGCCTGCTA | TATAACAAAC | TCTTGCTTTT | 600
| TCTACCAACA | TCCAGTTTTT | CTCCAGATCA | AGATGTTTTT | CCTTTTATA | ACAATTGGCA | 660
| GCAGCAAGAT | TAGCTATGAG | GGACCTGTTG | TCACCAGTGA | TGCATGCAGC | ACAAGTTCCT | 720
| GTTGGCTGCT | CATTCTGCTC | GTAGTAATGA | GCATCCACAT | GGGCTTCAGC | AGCTTTTCTC | 780
| TTCAGGATCT | CCCCAAATTT | ATCTATCCCA | ATGCATCCAA | AAATGTTGC | TGCTTTGTGT | 840
| GGCTGTTGAA | TCATCCACTG | AGCCACTTTA | ATTGAATTCT | GGGTAGAGCC | ACCAGCATGA | 900
| TATTCGACTT | TGAATTTTTT | CACAAGTTCA | TCAAACAGTT | CCTTGTGTTT | GTCTTCAGCC | 960
| AAGATTTGGT | CATTTGGTTT | CAGAGAATAC | TTATCAAGGA | AATCTTTGTC | CACTACAGCA | 1020
| GAGATGTCAA | GCAGAGGATT | TCCCATTCCA | AAGAGAATAT | TTTCTCTGAC | TGACGTCATG | 1080
| GCTTCGCCCT | CCTGCCCAGC | GCCACGGCGG | CCGCGTCCGA | TGCTCTACGT | CCGCTCGGGC | 1140
| AGCAGCAGGT | ACCACAGCAA | CTGCTTCCCG | GC | | | 1172

( 2 ) INFORMATION FOR SEQ ID NO: 7:

( i ) SEQUENCE CHARACTERISTICS:
        ( A ) LENGTH: 1181 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 51..1139

( i x ) FEATURE:
        ( A ) NAME/KEY: mat_peptide
        ( B ) LOCATION: 51..1136

( x i ) SEQUENCE DESCRIPTION: SEQ ID NO: 7:

```
GTGGATGGCA  GAGGTGGGCT  GTAGAGCCAA  AGTGGGGTGG  GAGCGCGAAG  ATG GCT                    56
                                                            Met Ala
                                                              1

GCT GCT GAG GAG GAG CCG AAG CCC AAA AAG CTG AAG GTG GAG GCG CCG                       104
Ala Ala Glu Glu Glu Pro Lys Pro Lys Lys Leu Lys Val Glu Ala Pro
        5              10                 15

CAA GCG CTG AGA GAA AAT ATT CTC TTT GGA ATG GGA AAT CCT CTG CTT                       152
Gln Ala Leu Arg Glu Asn Ile Leu Phe Gly Met Gly Asn Pro Leu Leu
 20                  25                  30

GAC ATC TCT GCT GTA GTG GAC AAA GAT TTC CTT GAT AAG TAT TCT CTG                       200
Asp Ile Ser Ala Val Val Asp Lys Asp Phe Leu Asp Lys Tyr Ser Leu
 35                  40                  45                  50
```

-continued

| | | | | | | | | | | | | | | | | |
|---|---|---|---|---|---|---|---|---|---|---|---|---|---|---|---|---|
| AAA | CCA | AAT | GAC | CAA | ATC | TTG | GCT | GAA | GAC | AAA | CAC | AAG | GAA | CTG | TTT | 248 |
| Lys | Pro | Asn | Asp | Gln<br>55 | Ile | Leu | Ala | Glu | Asp<br>60 | Lys | His | Lys | Glu | Leu<br>65 | Phe | |
| GAT | GAA | CTT | GTG | AAA | AAA | TTC | AAA | GTC | GAA | TAT | CAT | GCT | GGT | GGC | TCT | 296 |
| Asp | Glu | Leu | Val<br>70 | Lys | Lys | Phe | Lys | Val<br>75 | Glu | Tyr | His | Ala | Gly<br>80 | Gly | Ser | |
| ACC | CAG | AAT | TCA | ATT | AAA | GTG | GCT | CAG | TGG | ATG | ATT | CAA | CAG | CCA | CAC | 344 |
| Thr | Gln | Asn<br>85 | Ser | Ile | Lys | Val | Ala<br>90 | Gln | Trp | Met | Ile | Gln<br>95 | Gln | Pro | His | |
| AAA | GCA | GCA | ACA | TTT | TTT | GGA | TGC | ATT | GGG | ATA | GAT | AAA | TTT | GGG | GAG | 392 |
| Lys | Ala<br>100 | Ala | Thr | Phe | Phe | Gly<br>105 | Cys | Ile | Gly | Ile | Asp<br>110 | Lys | Phe | Gly | Glu | |
| ATC | CTG | AAG | AGA | AAA | GCT | GCT | GAA | GCC | CAT | GTG | GAT | GCT | CAT | TAC | TAC | 440 |
| Ile<br>115 | Leu | Lys | Arg | Lys<br>120 | Ala | Ala | Glu | Ala | His<br>125 | Val | Asp | Ala | His | Tyr<br>130 | Tyr | |
| GAG | CAG | AAT | GAG | CAG | CCA | ACA | GGA | ACT | TGT | GCT | GCA | TGC | ATC | ACT | GGT | 488 |
| Glu | Gln | Asn | Glu | Gln<br>135 | Pro | Thr | Gly | Thr | Cys<br>140 | Ala | Ala | Cys | Ile | Thr<br>145 | Gly | |
| GAC | AAC | AGG | TCC | CTC | ATA | GCT | AAT | CTT | GCT | GCT | GCC | AAT | TGT | TAT | AAA | 536 |
| Asp | Asn | Arg | Ser<br>150 | Leu | Ile | Ala | Asn | Leu<br>155 | Ala | Ala | Ala | Asn | Cys<br>160 | Tyr | Lys | |
| AAG | GAA | AAA | CAT | CTT | GAT | CTG | GAG | AAA | AAC | TGG | ATG | TTG | GTA | GAA | AAA | 584 |
| Lys | Glu | Lys<br>165 | His | Leu | Asp | Leu | Glu<br>170 | Lys | Asn | Trp | Met | Leu<br>175 | Val | Glu | Lys | |
| GCA | AGA | GTT | TGT | TAT | ATA | GCA | GGC | TTT | TTT | CTT | ACA | GTT | TCC | CCA | GAG | 632 |
| Ala | Arg<br>180 | Val | Cys | Tyr | Ile | Ala<br>185 | Gly | Phe | Phe | Leu | Thr<br>190 | Val | Ser | Pro | Glu | |
| TCA | GTA | TTA | AAG | GTG | GCT | CAC | CAT | GCT | TCT | GAA | AAC | AAC | AGG | ATT | TTC | 680 |
| Ser<br>195 | Val | Leu | Lys | Val | Ala<br>200 | His | His | Ala | Ser | Glu<br>205 | Asn | Asn | Arg | Ile | Phe<br>210 | |
| ACT | TTG | AAT | CTA | TCT | GCA | CCG | TTT | ATT | AGC | CAG | TTC | TAC | AAG | GAA | TCA | 728 |
| Thr | Leu | Asn | Leu | Ser<br>215 | Ala | Pro | Phe | Ile | Ser<br>220 | Gln | Phe | Tyr | Lys | Glu<br>225 | Ser | |
| TTG | ATG | AAA | GTT | ATG | CCT | TAT | GTT | GAT | ATA | CTT | TTT | GGA | AAT | GAG | ACA | 776 |
| Leu | Met | Lys | Val<br>230 | Met | Pro | Tyr | Val | Asp<br>235 | Ile | Leu | Phe | Gly | Asn<br>240 | Glu | Thr | |
| GAA | GCT | GCC | ACT | TTT | GCT | AGA | GAG | CAA | GGC | TTT | GAG | ACT | AAA | GAC | ATT | 824 |
| Glu | Ala | Ala<br>245 | Thr | Phe | Ala | Arg | Glu<br>250 | Gln | Gly | Phe | Glu | Thr<br>255 | Lys | Asp | Ile | |
| AAA | GAG | ATA | GCC | AAA | AAG | ACA | CAA | GCC | CTG | CCA | AAG | ATG | AAC | TCA | AAG | 872 |
| Lys | Glu<br>260 | Ile | Ala | Lys | Lys | Thr<br>265 | Gln | Ala | Leu | Pro | Lys<br>270 | Met | Asn | Ser | Lys | |
| AGG | CAG | CGA | ATC | GTG | ATC | TTC | ACC | CAA | GGG | AGA | GAT | GAC | ACT | ATA | ATG | 920 |
| Arg<br>275 | Gln | Arg | Ile | Val | Ile<br>280 | Phe | Thr | Gln | Gly | Arg<br>285 | Asp | Asp | Thr | Ile | Met<br>290 | |
| GCT | ACA | GAA | AGT | GAA | GTC | ACT | GCT | TTT | GCT | GTC | TTG | GAT | CAA | GAC | CAG | 968 |
| Ala | Thr | Glu | Ser | Glu<br>295 | Val | Thr | Ala | Phe | Ala<br>300 | Val | Leu | Asp | Gln | Asp<br>305 | Gln | |
| AAA | GAA | ATT | ATT | GAT | ACC | AAT | GGA | GCT | GGA | GAT | GCA | TTT | GTT | GGA | GGT | 1016 |
| Lys | Glu | Ile | Ile<br>310 | Asp | Thr | Asn | Gly | Ala<br>315 | Gly | Asp | Ala | Phe | Val<br>320 | Gly | Gly | |
| TTT | CTG | TCT | CAA | CTG | GTC | TCT | GAC | AAG | CCT | CTG | ACT | GAA | TGT | ATC | CGT | 1064 |
| Phe | Leu | Ser | Gln<br>325 | Leu | Val | Ser | Asp | Lys<br>330 | Pro | Leu | Thr | Glu | Cys<br>335 | Ile | Arg | |
| GCT | GGC | CAC | TAT | GCA | GCA | AGC | ATC | ATA | ATT | AGA | CGG | ACT | GGC | TGC | ACC | 1112 |
| Ala | Gly<br>340 | His | Tyr | Ala | Ala | Ser<br>345 | Ile | Ile | Ile | Arg | Arg<br>350 | Thr | Gly | Cys | Thr | |
| TTT | CCT | GAG | AAG | CCA | GAC | TTC | CAC | TGATGGAAGA | GCTGAAAACA | CAAGCCCAGG | | | | | | 1166 |
| Phe | Pro | Glu | Lys<br>355 | Pro | Asp | Phe | His<br>360 | | | | | | | | | |

AGTCAGACAC ACCCC                                                                1181

(2) INFORMATION FOR SEQ ID NO: 8:

(i) SEQUENCE CHARACTERISTICS:
        (A) LENGTH: 362 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Ala Ala Ala Glu Glu Pro Lys Pro Lys Lys Leu Lys Val Glu
 1               5                  10                  15

Ala Pro Gln Ala Leu Arg Glu Asn Ile Leu Phe Gly Met Gly Asn Pro
             20                  25                  30

Leu Leu Asp Ile Ser Ala Val Val Asp Lys Asp Phe Leu Asp Lys Tyr
             35                  40                  45

Ser Leu Lys Pro Asn Asp Gln Ile Leu Ala Glu Lys His Lys Glu
         50                  55                  60

Leu Phe Asp Glu Leu Val Lys Lys Phe Lys Val Glu Tyr His Ala Gly
 65                  70                  75                  80

Gly Ser Thr Gln Asn Ser Ile Lys Val Ala Gln Trp Met Ile Gln Gln
                 85                  90                  95

Pro His Lys Ala Ala Thr Phe Phe Gly Cys Ile Gly Ile Asp Lys Phe
             100                 105                 110

Gly Glu Ile Leu Lys Arg Lys Ala Glu Ala His Val Asp Ala His
             115                 120                 125

Tyr Tyr Glu Gln Asn Glu Gln Pro Thr Gly Thr Cys Ala Ala Cys Ile
130                 135                 140

Thr Gly Asp Asn Arg Ser Leu Ile Ala Asn Leu Ala Ala Ala Asn Cys
145                 150                 155                 160

Tyr Lys Lys Glu Lys His Leu Asp Leu Glu Lys Asn Trp Met Leu Val
                 165                 170                 175

Glu Lys Ala Arg Val Cys Tyr Ile Ala Gly Phe Phe Leu Thr Val Ser
             180                 185                 190

Pro Glu Ser Val Leu Lys Val Ala His His Ala Ser Glu Asn Asn Arg
             195                 200                 205

Ile Phe Thr Leu Asn Leu Ser Ala Pro Phe Ile Ser Gln Phe Tyr Lys
210                 215                 220

Glu Ser Leu Met Lys Val Met Pro Tyr Val Asp Ile Leu Phe Gly Asn
225                 230                 235                 240

Glu Thr Glu Ala Ala Thr Phe Ala Arg Glu Gln Gly Phe Glu Thr Lys
             245                 250                 255

Asp Ile Lys Glu Ile Ala Lys Lys Thr Gln Ala Leu Pro Lys Met Asn
             260                 265                 270

Ser Lys Arg Gln Arg Ile Val Ile Phe Thr Gln Gly Arg Asp Asp Thr
         275                 280                 285

Ile Met Ala Thr Glu Ser Glu Val Thr Ala Phe Ala Val Leu Asp Gln
     290                 295                 300

Asp Gln Lys Glu Ile Ile Asp Thr Asn Gly Ala Gly Asp Ala Phe Val
305                 310                 315                 320

Gly Gly Phe Leu Ser Gln Leu Val Ser Asp Lys Pro Leu Thr Glu Cys
                 325                 330                 335

Ile Arg Ala Gly His Tyr Ala Ala Ser Ile Ile Ile Arg Arg Thr Gly
             340                 345                 350
```

Cys Thr Phe Pro Glu Lys Pro Asp Phe His
    355                 360

( 2 ) INFORMATION FOR SEQ ID NO: 9:

( i ) SEQUENCE CHARACTERISTICS:
        ( A ) LENGTH: 1181 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO: 9:

```
GGGGTGTGTC TGACTCCTGG GCTTGTGTTT TCAGCTCTTC CATCAGTGGA AGTCTGGCTT      60
CTCAGGAAAG GTGCAGCCAG TCCGTCTAAT TATGATGCTT GCTGCATAGT GGCCAGCACG     120
GATACATTCA GTCAGAGGCT TGTCAGAGAC CAGTTGAGAC AGAAAACCTC CAACAAATGC     180
ATCTCCAGCT CCATTGGTAT CAATAATTTC TTTCTGGTCT TGATCCAAGA CAGCAAAAGC     240
AGTGACTTCA CTTTCTGTAG CCATTATAGT GTCATCTCTC CCTTGGGTGA AGATCACGAT     300
TCGCTGCCTC TTTGAGTTCA TCTTTGGCAG GGCTTGTGTC TTTTTGGCTA TCTCTTTAAT     360
GTCTTTAGTC TCAAAGCCTT GCTCTCTAGC AAAAGTGGCA GCTTCTGTCT CATTTCCAAA     420
AAGTATATCA ACATAAGGCA TAACTTTCAT CAATGATTCC TTGTAGAACT GGCTAATAAA     480
CGGTGCAGAT AGATTCAAAG TGAAAATCCT GTTGTTTTCA GAAGCATGGT GAGCCACCTT     540
TAATACTGAC TCTGGGGAAA CTGTAAGAAA AAAGCCTGCT ATATAACAAA CTCTTGCTTT     600
TTCTACCAAC ATCCAGTTTT TCTCCAGATC AAGATGTTTT TCCTTTTTAT AACAATTGGC     660
AGCAGCAAGA TTAGCTATGA GGGACCTGTT GTCACCAGTG ATGCATGCAG CACAAGTTCC     720
TGTTGGCTGC TCATTCTGCT CGTAGTAATG AGCATCCACA TGGGCTTCAG CAGCTTTTCT     780
CTTCAGGATC TCCCCAAATT TATCTATCCC AATGCATCCA AAAAATGTTG CTGCTTTGTG     840
TGGCTGTTGA ATCATCCACT GAGCCACTTT AATTGAATTC TGGGTAGAGC CACCAGCATG     900
ATATTCGACT TTGAATTTTT TCACAAGTTC ATCAAACAGT TCCTTGTGTT TGTCTTCAGC     960
CAAGATTTGG TCATTTGGTT TCAGAGAATA CTTATCAAGG AAATCTTTGT CCACTACAGC    1020
AGAGATGTCA AGCAGAGGAT TTCCCATTCC AAAGAGAATA TTTTCTCTCA GCGCTTGCGG    1080
CGCCTCCACC TTCAGCTTTT TGGGCTTCGG CTCCTCCTCA GCAGCAGCCA TCTTCGCGCT    1140
CCCACCCCAC TTTGGCTCTA CAGCCCACCT CTGCCATCCA C                       1181
```

( 2 ) INFORMATION FOR SEQ ID NO: 10:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 10:

Lys Thr Gln Ala Leu Pro Lys Val Asn Ser Lys Arg
1               5                   10

( 2 ) INFORMATION FOR SEQ ID NO: 11:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Modified-site
    ( B ) LOCATION: 5, 21, 25
    ( D ) OTHER INFORMATION: /label=Xaa
        / note= "Xaa = Unknown"

( x i ) SEQUENCE DESCRIPTION: SEQ ID NO: 11:

```
Lys  Phe  Lys  Val  Xaa  Tyr  His  Ala  Gly  Gly  Ser  Thr  Gln  Asn  Ser  Met
1                  5                       10                            15
Lys  Val  Ala  Gln  Xaa  Met  Ile  Gln  Xaa  Pro
              20                  25
```

( 2 ) INFORMATION FOR SEQ ID NO: 12:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 12:

```
Ala  Ala  Thr  Phe  Phe  Gly  His  Ile  Gly  Ile  Asp  Lys  Phe  Gly  Glu  Ile
1                  5                       10                            15
Leu  Lys  Ser  Lys  Ala  Ala  Asp  Ala  His  Val  Asp  Ala
              20                  25
```

( 2 ) INFORMATION FOR SEQ ID NO: 13:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 7, 11
        ( D ) OTHER INFORMATION: /label=Xaa
            / note= "Xaa = Unknown"

( x i ) SEQUENCE DESCRIPTION: SEQ ID NO: 13:

```
Thr  Phe  Thr  Leu  Asn  Leu  Xaa  Ala  Pro  Phe  Ile  Xaa  Gln  Phe  Phe  Lys
1                  5                       10                            15
Glu  Ala  Leu
```

( 2 ) INFORMATION FOR SEQ ID NO: 14:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 14:

```
Ala  Gly  His  Tyr  Ala  Ala  Ser  Val  Ile  Ile  Arg
1                  5                       10
```

( 2 ) INFORMATION FOR SEQ ID NO: 15:

( i ) SEQUENCE CHARACTERISTICS:

(A) LENGTH: 8 amino acids
(B) TYPE: amino acid
(C) STRANDEDNESS: unknown
(D) TOPOLOGY: unknown (ii) MOLECULE TYPE: peptide (ix) FEATURE:
(A) NAME/KEY: Modified-site
(B) LOCATION: 5
(D) OTHER INFORMATION: /label=Xaa
/ note= "Xaa = Uknown"

(xi) SEQUENCE DESCRIPTION: SEQ ID NO: 15:

Lys Phe Lys Val Xaa Tyr His Ala
1               5

(2) INFORMATION FOR SEQ ID NO: 16:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: modified_base
(B) LOCATION: 12
(C) IDENTIFICATION METHOD: experimental
(D) OTHER INFORMATION: /evidence=EXPERIMENTAL
/ mod_base= i
/ note= "N = inosine"

(ix) FEATURE:
(A) NAME/KEY: modified_base
(B) LOCATION: 13
(C) IDENTIFICATION METHOD: experimental
(D) OTHER INFORMATION: /evidence=EXPERIMENTAL
/ mod_base= i
/ note= "N = Inosine"

(ix) FEATURE:
(A) NAME/KEY: modified_base
(B) LOCATION: 14
(C) IDENTIFICATION METHOD: experimental
(D) OTHER INFORMATION: /evidence=EXPERIMENTAL
/ mod_base= i
/ note= "N = inosine"

(ix) FEATURE:
(A) NAME/KEY: modified_base
(B) LOCATION: 15
(C) IDENTIFICATION METHOD: experimental
(D) OTHER INFORMATION: /evidence=EXPERIMENTAL
/ mod_base= i
/ note= "N = Inosine"

(xi) SEQUENCE DESCRIPTION: SEQ ID NO: 16:

AARTTYAARG TNNNNTAYCA YGC                                    23

(2) INFORMATION FOR SEQ ID NO: 17:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 17:

Gln Phe Phe Lys Glu Ala
1               5

( 2 ) INFORMATION FOR SEQ ID NO: 18:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 18:

GTYAARAARTTYCTYCG      17

( 2 ) INFORMATION FOR SEQ ID NO: 19:

( i ) SEQUENCE CHARACTERISTICS:
        ( A ) LENGTH: 154 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO: 19:

| Lys | Phe | Lys | Val | Gly | Tyr | His | Ala | Gly | Gly | Ser | Thr | Gln | Asn | Ser | Met |
| 1 | | | | 5 | | | | | 10 | | | | | 15 | |
| Lys | Val | Ala | Gln | Trp | Met | Ile | Gln | Glu | Pro | His | Arg | Ala | Ala | Thr | Phe |
| | | | 20 | | | | 25 | | | | | 30 | | | |
| Phe | Gly | Cys | Ile | Gly | Ile | Asp | Lys | Phe | Gly | Glu | Ile | Leu | Lys | Ser | Lys |
| | | 35 | | | | | 40 | | | | | 45 | | | |
| Ala | Ala | Asp | Ala | His | Val | Asp | Ala | His | Tyr | Tyr | Glu | Gln | Asn | Glu | Gln |
| 50 | | | | | 55 | | | | | 60 | | | | | |
| Pro | Thr | Gly | Thr | Cys | Ala | Ala | Cys | Ile | Thr | Gly | Gly | Asn | Arg | Ser | Leu |
| 65 | | | | 70 | | | | | 75 | | | | | 80 | |
| Val | Ala | Asn | Leu | Ala | Ala | Ala | Asn | Cys | Tyr | Xaa | Lys | Glu | Xaa | His | Leu |
| | | | | 85 | | | | 90 | | | | | | 95 | |
| Asp | Leu | Glu | Asn | Asn | Trp | Met | Leu | Val | Glu | Lys | Ala | Arg | Val | Tyr | Tyr |
| | | | 100 | | | | | 105 | | | | | 110 | | |
| Ile | Ala | Gly | Phe | Phe | Leu | Thr | Val | Ser | Pro | Glu | Ser | Val | Leu | Lys | Val |
| | | 115 | | | | | 120 | | | | | 125 | | | |
| Ala | Arg | Tyr | Ala | Ala | Glu | Asn | Asn | Arg | Thr | Phe | Thr | Leu | Asn | Pro | Ser |
| | 130 | | | | | 135 | | | | | 140 | | | | |
| Ala | Pro | Phe | Ile | Ser | Gln | Phe | Phe | Lys | Glu | | | | | | |
| 145 | | | | | 150 | | | | | | | | | | |

( 2 ) INFORMATION FOR SEQ ID NO: 20:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 20:

GAATTCGTGG AGCCAAACCG CGG      23

( 2 ) INFORMATION FOR SEQ ID NO: 21:

( i ) SEQUENCE CHARACTERISTICS:
        ( A ) LENGTH: 22 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO: 21:

AGAGTCAAGA TGGCAGCTGC GG        22

( 2 ) INFORMATION FOR SEQ ID NO: 22:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 22:

GTCTCTGCAG TCTCCACTCC        20

( 2 ) INFORMATION FOR SEQ ID NO: 23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 23:

GCCTGAGTTG CTTTTCTTCC G        21

( 2 ) INFORMATION FOR SEQ ID NO: 24:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 24:

AATGATGCTG CTTTGTGTGG        20

( 2 ) INFORMATION FOR SEQ ID NO: 25:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 25:

TTGAATCATC CACTGAGCCA        20

( 2 ) INFORMATION FOR SEQ ID NO: 26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 26:

GTGGATGGCA GAGGTGGGCT G 21

( 2 ) INFORMATION FOR SEQ ID NO: 27:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 27:

GCCAAAGTGG GGTGGGAGCG CG 22

( 2 ) INFORMATION FOR SEQ ID NO: 28:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 28:

GCCGGGAAGC AGTTGCTGTG G 21

( 2 ) INFORMATION FOR SEQ ID NO: 29:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 29:

GCTGCTGCCC GAGCGGACGT AG 22

( 2 ) INFORMATION FOR SEQ ID NO: 30:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 30:

GGGGTGTCTG CACTCCTGGG 20

( 2 ) INFORMATION FOR SEQ ID NO: 31:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 31:

CTTGTGTTTT CAGCTCTTCC 20

( 2 ) INFORMATION FOR SEQ ID NO: 32:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 32:

GTAACCTGCC ATGGCTCATA TGACGTCAGT CAGAGAAATA TTC        43

( 2 ) INFORMATION FOR SEQ ID NO: 33:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 33:

GGGGTGGGAG CGCGCATATG GCTGCTGCTG AGGAGGAG        38

( 2 ) INFORMATION FOR SEQ ID NO: 34:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 34:

AGTTCTACAA CGAATCATTG        20

What is claimed is:

1. An isolated and purified polynucleotide comprising a nucleotide sequence consisting of a nucleotide sequence selected from the group consisting of:

a) the sequence of SEQ ID NO: 1, the sequence of SEQ ID NO:4, or the sequence of SEQ ID NO: 7;

b) sequences that are complementary to the sequences of (a); and c) sequences that, on expression, encode a polypeptide encoded by the sequences of (a).

2. The polynucleotide of claim 1 that is a DNA molecule.

3. The polynucleotide of claim 1 that is an RNA molecule.

4. The polynucleotide of claim 2 wherein the nucleotide sequence is SEQ ID NO: 1, 4, or 7.

5. An oligonucleotide of 15 nucleotides to about 50 nucleotides containing a nucleotide sequence of at least 15 nucleotides that is identical or complementary to a contiguous sequence of the polynucleotide selected from the group consisting of SEQ ID NO: 1 from nucleotide position 16 to nucleotide position 1098 and sequences that on expression, encode a polypeptide encoded by the sequence of SEQ ID NO: 1.

6. An oligonucleotide of 15 nucleotides to about 50 nucleotides containing a nucleotide sequence of at least 15 nucleotides that is identical or complementary to a contiguous sequence of the polynucleotide selected from the group consisting of SEQ ID NO: 4 and sequences that on expression, encode a polypeptide encoded by the sequence of SEQ ID NO: 4.

7. An oligonucleotide fragment of the polynucleotide of SEQ ID NO: 7 consisting of at least 15 nucleotides that is identical or complementary to the nucleotide sequence of SEQ ID NO: 7.

8. The oligonucleotide of claims 5, 6 or 7 that is an antisense oligonucleotide.

9. An expression vector comprising the DNA molecule of claim 4.

10. The expression vector of claim further comprising an enhancer-promoter operatively linked to the polynucleotide.

11. The expression vector of claim 9 wherein the polynucleotide has the nucleotide sequence of SEQ ID NO: 1, the sequence of SEQ ID NO: 4, or the sequence of SEQ ID NO:7.

12. A host cell transformed with the expression vector of claim 9.

13. The transformed host cell of claim 12 that is a eukaryotic host cell.

14. The transformed host cell of claim 12 that is a bacterial cell.

15. The transformed host cell of claim 14 wherein the bacterial cell is an E. coli.

16. The transformed host cell of claim 15 wherein the E. coli is designated BL21(DE3)/pET21AK5, BL21(DE3)/ pET21AK 18, HMS174(DE3)/pET21AK5 or HMS174 (DE3)/pET21AK 18.

17. A process of making adenosine kinase comprising transforming a host cell with the expression vector of claim 9, maintaining the transformed cell for a period of time sufficient for expression of the adenosine kinase and recovering the adenosine kinase.

18. The process of claim 17 wherein the polynucleotide has the nucleotide sequence of SEQ ID NO: 1, the sequence of SEQ ID NO: 4, or the sequence of SEQ ID NO:7.

19. The process of claim 17 wherein the adenosine kinase is human adenosine kinase.

20. The process of claim 17 wherein the host cell is a eukaryotic host cell.

21. The process of claim 20 wherein the host cell is a bacterial cell.

22. The process of claim 21 wherein the bacterial cell is an *E. coli*.

* * * * *

UNITED STATES PATENT AND TRADEMARK OFFICE
CERTIFICATE OF CORRECTION

PATENT NO. : 5,861,294
DATED : January 19, 1999
INVENTOR(S) : Cowart et al.

It is certified that error appears in the above-identified patent and that said Letters Patent is hereby corrected as shown below:

Column 50, line 51, change "claim further" to --claim 9 further--.

Signed and Sealed this

Eighth Day of June, 1999

Attest:

Q. TODD DICKINSON

*Attesting Officer*            Acting Commissioner of Patents and Trademarks